(12) United States Patent
Lecchini et al.

(10) Patent No.: US 12,279,685 B2
(45) Date of Patent: Apr. 22, 2025

(54) FLUID DISPENSER FOR DISPENSING A COSMETIC PRODUCT

(71) Applicants: Hülya Topal Lecchini, Zug (CH); Stefano Lecchini, Zug (CH)

(72) Inventors: Hülya Topal Lecchini, Zug (CH); Stefano Lecchini, Zug (CH)

( * ) Notice: Subject to any disclaimer, the term of this patent is extended or adjusted under 35 U.S.C. 154(b) by 773 days.

(21) Appl. No.: 17/423,703

(22) PCT Filed: Feb. 7, 2020

(86) PCT No.: PCT/EP2020/053152
§ 371 (c)(1),
(2) Date: Jul. 16, 2021

(87) PCT Pub. No.: WO2020/161310
PCT Pub. Date: Aug. 13, 2020

(65) Prior Publication Data
US 2022/0117372 A1    Apr. 21, 2022

(30) Foreign Application Priority Data
Feb. 8, 2019   (EP) ..................... 19156201

(51) Int. Cl.
*A45D 34/04*   (2006.01)
*A45D 40/24*   (2006.01)
(Continued)

(52) U.S. Cl.
CPC ............. *A45D 34/04* (2013.01); *A45D 40/24* (2013.01); *A61K 8/922* (2013.01); *B05B 7/2443* (2013.01);
(Continued)

(58) Field of Classification Search
CPC .. A45D 34/04; A45D 40/24; A45D 2200/055; A45D 2200/057;
(Continued)

(56) References Cited

U.S. PATENT DOCUMENTS

| 9,375,742 B1 | 6/2016 | Yoked |
| 2007/0125882 A1 | 6/2007 | Schwal et al. |

(Continued)

FOREIGN PATENT DOCUMENTS

| CN | 1871073 A | 11/2006 |
| CN | 101111438 A | 1/2008 |

(Continued)

OTHER PUBLICATIONS

Office Action issued Jun. 27, 2023 in Japanese Application No. 2021-545994.

(Continued)

*Primary Examiner* — Jeremy Carroll
(74) *Attorney, Agent, or Firm* — Sughrue Mion, PLLC

(57) ABSTRACT

A fluid dispenser (1) for dispensing a cosmetic composition (2) comprises a housing (3), a dispenser head (4), at least one first receptacle (16) being connectable to a first reservoir (5) comprising a first fluid (6), and at least one second receptacle (17) being connectable or connected to a second reservoir (7), the second reservoir (7) being configured to receive a second fluid (8). The fluid dispenser (1) further comprises a mixing area (18) being in fluid communication with the dispenser head (4), the first receptacle (16) and the second receptacle (17). The mixing area (18) is configured such, that the cosmetic composition (2) is generated when a dose of the first fluid (6) is mixed with the second fluid (8) within the mixing area (18).

33 Claims, 15 Drawing Sheets

(51) Int. Cl.
*A61K 8/92* (2006.01)
*B05B 7/24* (2006.01)
*B05B 12/14* (2006.01)
*B05B 17/06* (2006.01)

(52) U.S. Cl.
CPC ........ *B05B 7/2464* (2013.01); *B05B 12/1409* (2013.01); *B05B 12/1418* (2013.01); *B05B 17/0607* (2013.01); *A45D 2200/055* (2013.01); *A45D 2200/057* (2013.01); *A45D 2200/058* (2013.01); *A61K 2800/87* (2013.01)

(58) Field of Classification Search
CPC .............. A45D 2200/058; A61K 8/922; A61K 2800/87; B05B 7/2443; B05B 7/2464; B05B 12/1409; B05B 12/1418; B05B 17/0607
See application file for complete search history.

(56) References Cited

U.S. PATENT DOCUMENTS

| | | |
|---|---|---|
| 2008/0001002 A1 | 1/2008 | Garon |
| 2010/0205732 A1 | 8/2010 | Mühlhausen et al. |
| 2012/0205464 A1* | 8/2012 | Pardonge ............ B05B 17/0607 239/102.1 |
| 2013/0101500 A1 | 4/2013 | Nikolov et al. |
| 2014/0197244 A1 | 7/2014 | Quellet |
| 2015/0352576 A1 | 12/2015 | Burrowes et al. |
| 2017/0121070 A1* | 5/2017 | Baumann ............ B65D 83/0055 |

FOREIGN PATENT DOCUMENTS

| | | | | |
|---|---|---|---|---|
| CN | 103037976 A | 4/2013 | | |
| CN | 106413909 A | 2/2017 | | |
| DE | 202 08 173 U1 | 9/2002 | | |
| EP | 1 023 125 B1 | 5/2003 | | |
| EP | 3 751 576 A1 | 12/2020 | | |
| JP | 3-12578 U | 2/1991 | | |
| JP | 6-100049 A | 4/1994 | | |
| JP | 2005-505505 A | 2/2005 | | |
| JP | 6402284 B1 | 10/2018 | | |
| KR | 2001-0031100 A | 4/2001 | | |
| KR | 10-2013-0115297 A | 10/2013 | | |
| WO | WO-9530491 A1 * | 11/1995 | .......... | B01F 15/0237 |
| WO | 02/094423 A1 | 11/2002 | | |
| WO | 2008/053311 A2 | 5/2008 | | |
| WO | WO-2012129318 A2 * | 9/2012 | ......... | B05B 11/0054 |
| WO | WO-2014036493 A2 * | 3/2014 | ......... | B05B 11/0039 |
| WO | 2017/075024 A1 | 5/2017 | | |
| WO | 2020/260906 A1 | 12/2020 | | |

OTHER PUBLICATIONS

International Search Report for PCT/EP2020/053152 dated, May 15, 2020 (PCT/ISA/210).
Written Opinion of the International Searching Authority for PCT/EP2020/053152 (PCT/ISA/237).
Office Action issued Sep. 27, 2023 in Korean Application No. 10-2021-7026612.
Office Action dated Jul. 5, 2022 from the China National Intellectual Property Administration in CN Application No. 202080012890.1.

* cited by examiner

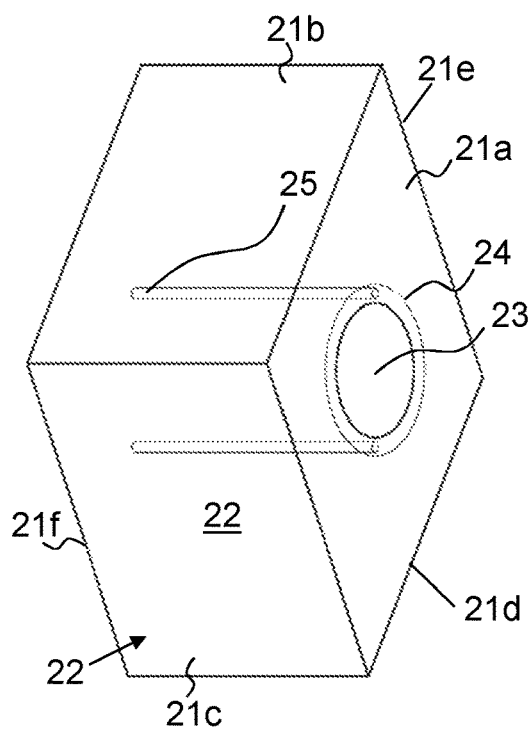 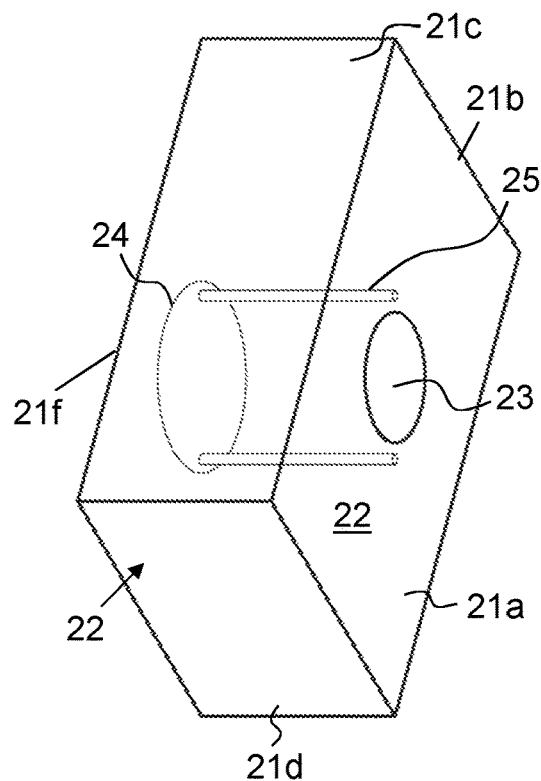
FIG. 7a  FIG. 7b
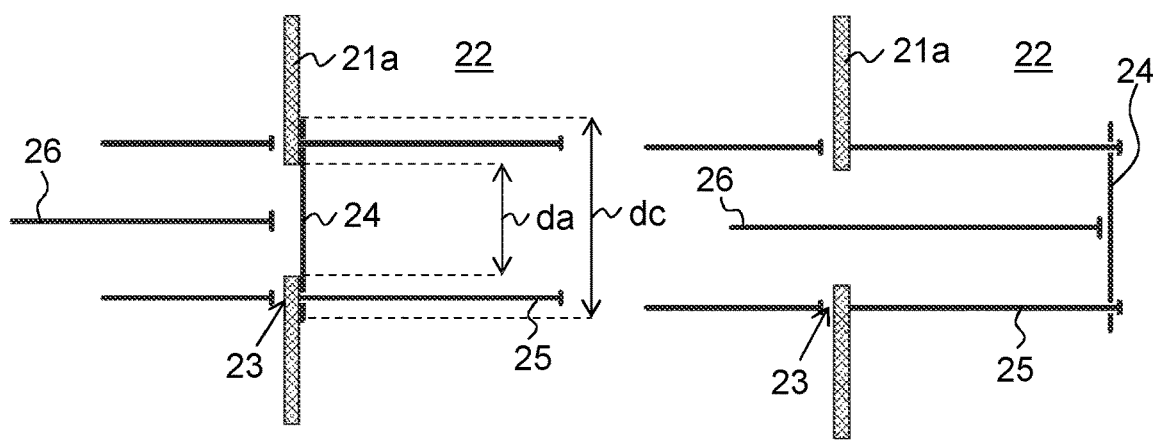
FIG. 8a  FIG. 8b

FLUID DISPENSER FOR DISPENSING A COSMETIC PRODUCT

CROSS REFERENCE TO RELATED APPLICATIONS

This application is a National Stage of International Application No. PCT/EP2020/053152 filed Feb. 7, 2020, claiming priority based on European Patent Application No. 19 156 201.6 filed Feb. 8, 2019.

TECHNICAL FIELD

The present invention relates to a fluid dispenser for dispensing a cosmetic composition, a method of producing a fluid dispenser, as well as to a reservoir for use in such a fluid dispenser and the use of a reservoir in such a fluid dispenser.

PRIOR ART

Traditionally a perfume relates to a solution of fragrance or aroma compounds that are dissolved or dispersed in selected solvents. A very common solvent used in perfumery products is ethanol or a mix of water and ethanol. However, the presence of ethanol in perfumery products prevents people with sensitive skin or children from using such products. There are also alcohol-free fragrance products available, such as oil-based perfumes for example. These perfumes comprise one or more oils combined with a fragrance. One of the disadvantages with these products is that their appliance might result in greasy stains and can render surfaces they are applied onto sticky. It is also known to encapsulate the fragrances in suitable compositions such as in a mixture of lipid, phospholipid and polymer matrix. However, the manufacturing of such encapsulated fragrances is rather cumbersome. Moreover, since the complete usage of a perfume may take months or even years the achievement of a stable fragrance dispersion in the aqueous solution and an adequate storage preventing a decomposition or vaporization of the perfume are crucial aspects, as well.

Notwithstanding the above existing perfume dispensers are generally designed as disposable products which are disposed after their content has been used. Consequently, such dispensers are undesirable in view of environmental aspects. Moreover, the applicable product, i.e. the perfume, is present in the perfume dispenser as a ready to-use product. As such it has to be carried along by a user in its entirety, which can be impractical for travelers.

Last but not least users have to buy different dispensers if they want either solutions with a different perfume concentration (e.g. "eau de parfum" versus "eau de toilette") or different fragrances and/or aroma compounds (e.g. "Chanel No. 5" versus "Chanel Égoïste").

SUMMARY OF THE INVENTION

It is an object of the present invention to remedy the drawbacks of the prior art. In particular, it is an object of the present invention to provide a fluid dispenser for dispensing a cosmetic product, in particular a perfume dispenser, which is improved with respect to the generation and the storage of the cosmetic composition to be dispensed.

A fluid dispenser, in particular a perfume dispenser, for dispensing a cosmetic composition, in particular a perfume, is provided, which comprises a housing, a dispenser head being arranged on the housing, at least one first receptacle being provided in the housing, and at least one second receptacle being provided in the housing. The dispenser head is configured to dispense the cosmetic composition from the fluid dispenser. The first receptacle is connectable to a first reservoir comprising a first fluid, and the second receptacle is connectable or connected to a second reservoir, the second reservoir being configured to comprise a second fluid. The fluid dispenser further comprises a mixing area being in fluid communication with the dispenser head, the first receptacle and the second receptacle. The mixing area is configured such, that the cosmetic composition is generated when a dose of the first fluid is mixed with the second fluid within the mixing area.

Since the mixing area of the fluid dispenser is in fluid communication with the first and the second receptacle, respectively, a first fluid provided in a first reservoir which is in turn in connection with the first receptacle and a second fluid provided in a second reservoir which is in turn in connection with the second receptacle can be conducted from the respective receptacles to the mixing area. Moreover, since the mixing area is also in fluid communication with the dispenser head the thus generated cosmetic composition can then be conducted from the mixing area to the dispenser head. That is, the fluids required and/or desired for the preparation of the cosmetic composition are provided in separate reservoirs. Said fluids are then mixed with each other or dispersed one within the other in the mixing area, whereupon the cosmetic product is generated. The fluid dispenser in accordance with the invention thus enables the generation of the cosmetic product on demand. The disadvantages associated with the storage and stability of a ready-to-use cosmetic composition as mentioned above are thereby overcome.

It is preferred that the fluid dispenser is configured such, that the cosmetic product is generated essentially immediately before it is dispensed. In the context of the present invention essentially immediately means that the cosmetic product is generated from the first and second fluids during the period of application of the dispenser by a user. This means that if a user wishes to apply the cosmetic composition he will activate an activation device of the dispenser (see further below), whereupon the cosmetic composition is generated from the first and second fluids and immediately after its generation is dispensed from the dispenser. Said period of application is typically in the range of some seconds or even less, preferably in the range of some microseconds to milliseconds.

The fluid dispenser can be provided with exactly two receptacles or with more than two receptacles. For the reasons of simplicity reference is made herein to a fluid dispenser comprising two receptacles only. However, it should be noted that explanations provided with regard to the fluid dispenser comprising two receptacles likewise apply to a fluid dispenser comprising three or more receptacles.

The dispenser head preferably corresponds to an atomizer, such that the generated cosmetic composition, once it is generated, can be sprayed from the dispenser and applied onto a user.

In order that a dose of the first fluid can be mixed with the second fluid within the mixing area it is preferred that the fluid dispenser, for example the first receptacle and/or the first reservoir or further components of the fluid dispenser are configured to deliver a dose of the first fluid to the mixing area. A dose of the first fluid means a preferably pre-selected quantity or amount of the first fluid. To this end it is likewise preferred that a dose of the second fluid is mixed with a dose of the first fluid within the mixing area.

The fluid dispenser, in particular the mixing area or further components of the fluid dispenser, can be configured to generate droplets of the first fluid. That is, if a quantity or amount of the first fluid is provided from the first receptacle to the mixing area in the form of a continuous liquid flow, said continuous liquid flow will be divided or split into droplets. It is however also conceivable that the first reservoir and/or the first receptacle are configured such, that the first fluid is provided to the mixing area already in the form of droplets. In this case the mixing area effectuates that the droplets of the first fluid remain droplets. The spatial dimension of the droplets delivered to the mixing area and the droplets generated in the mixing area can be the same or different. For example, it is conceivable that droplets having a certain diameter are delivered to the mixing area and that the mixing area then effectuates a reduction of the droplet diameter, i.e. the mixing area generates droplets of a smaller size. In the following, various aspects regarding the generation of a dose of the first fluid and/or a dose of the second fluid as well as the generation of droplets will be discussed in detail.

Namely, in a first aspect, the fluid dispenser can further comprise at least a dispensing arrangement, and at least a first dosing arrangement and/or at least a second dosing arrangement. The dispensing arrangement is configured to actuate the first dosing arrangement and/or the second dosing arrangement upon its actuation. That is, the dispensing arrangement is configured to be actuated by a user of the fluid dispenser, whereupon it actuates the first dosing arrangement and/or the second dosing arrangement. If a first dosing arrangement is present in the fluid dispenser, the first dosing arrangement is in fluid communication with the first receptacle and the mixing area. Likewise, if a second dosing arrangement is present in the fluid dispenser, the second dosing arrangement is in fluid communication with the second receptacle and the mixing area. The first dosing arrangement is configured to generate upon actuation by the dispensing arrangement, preferably upon receipt of a first dosing arrangement trigger signal that is produced by the dispensing arrangement, the dose of the first fluid. Likewise, the second dosing arrangement is configured to generate upon actuation by the dispensing arrangement, preferably upon receipt of a second dosing arrangement trigger signal that is produced by the dispensing arrangement, a dose of the second fluid.

The dispensing arrangement can be configured such, that the first dosing arrangement and the second dosing arrangement are actuated simultaneously or temporally delayed with respect to one another. For example, the dispensing arrangement can be configured such that the first dosing arrangement trigger signal and the second dosing arrangement trigger signal are produced by the dispensing arrangement simultaneously or temporally delayed with respect to one another. If the first and second dosing arrangement are actuated at different points in time, a time difference between the first point in time and the second point in time can be in the range of microseconds to milliseconds within a dispensing cycle, as will be explained in greater detail below.

The dispensing arrangement is preferably configured such, that the mixing area comprises both the first fluid and the second fluid only in the event that the dispensing arrangement has been actuated. In other words, it is preferred that the cosmetic composition is generated only in the event that the dispensing arrangement has been actuated.

Again in other words, it is preferred that the mixing area does at least not comprise the first fluid if the dispensing arrangement has not been actuated by the user. It is even conceivable that the dispensing arrangement is configured such, that neither the first fluid nor the second fluid are present in the mixing area if the dispensing arrangement has not been actuated. Hence, if the dispensing arrangement is in a rest state, e.g. after the cosmetic composition has been dispensed, neither first fluid nor second fluid is present in the mixing area, or, and as will be explained in greater detail below, only second fluid but no first fluid is present in the mixing area. To this end it should be noted that a presence or absence of the first fluid and, if applicable, of the second fluid refers to these fluids in any form, e.g. fluid in the form of droplets or "continuous", i.e. in non-droplet form.

The dispensing arrangement is preferably further configured to transfer the cosmetic composition from the mixing area to the dispenser head for dispensing. That is to say, the dispensing arrangement can perform a dual-function. Namely, it can be configured to actuate the first and second dosing arrangements such that doses of the first and second fluid are generated, and it can further be configured to transfer the cosmetic composition from the mixing area to the dispenser head for dispensing.

The dispensing arrangement can be configured such, that an actuation of the first dosing arrangement and/or of the second dosing arrangement in order to generate the dose of the first fluid and/or the dose of the second fluid occurs in a first step and the transfer of the cosmetic composition from the mixing area to the dispenser head occurs in a second step taking place after the first step as seen in time.

For example, it is conceivable that the first dosing arrangement and the second dosing arrangement are simultaneously actuated by the dispensing arrangement and within the same dispensing cycle. Thereafter, a transfer of the cosmetic composition from the mixing area to the dispenser head can be effectuated by the dispensing arrangement. It is conceivable that an actuation of the dosing arrangement(s) takes place before a transfer of the cosmetic composition. A dispensing cycle is understood here as a process comprising the actuation of the first dosing arrangement so as to generate the dose of the first fluid, which dose will then flow into the mixing area, and the transfer of the cosmetic composition from the mixing area to the dispenser head. However, it is likewise conceivable that the first dosing arrangement is actuated by the dispensing arrangement at first, wherein the second dosing arrangement is subsequently actuated by the dispensing arrangement, or vice versa. That is, an actuation of the first and second dosing arrangements takes place on a staggered basis. Then, after an actuation of both dosing arrangements, a transfer of the cosmetic composition from the mixing area to the dispenser head is effectuated by the dispensing arrangement. To this end, different scenarios can be distinguished. Firstly, it is conceivable that a staggered actuation of the first dosing arrangement and the second dosing arrangement takes place within the same dispensing cycle. An actuation of the first dosing arrangement and of the second dosing arrangement within the same dispensing cycle means that, in an initial state of the dispensing cycle, neither first nor second fluid is present in the mixing area. If a user wants to apply the cosmetic composition, he actuates the dispensing arrangement in a first step, wherein doses of the first fluid and of the second fluid are generated by the corresponding dosing arrangements, and wherein said doses will flow into the mixing area so as to generate the cosmetic composition in the mixing area. Once that the cosmetic composition is generated, it can be dispensed from the fluid dispenser in a second step taking place after the first step. Secondly, it is conceivable that the staggered actuation of the first dosing arrangement and the second dosing arrangement takes place during two subsequent dispensing cycles. In this case, and as will be explained in greater detail below, in an initial state of the dispensing cycle, a dose of the second fluid has already been generated. If a user wants to apply the cosmetic composition, he actuates the dispensing arrangement in a first step, wherein a dose of the first fluid is generated by the first dosing arrangement, and wherein said dose will flow into the mixing area so as to mix with the dose of the second fluid, whereby the cosmetic composition is generated in the mixing area. Once that the cosmetic composition is generated, it can be dispensed from the fluid dispenser in a second step taking place after the first step.

The dispensing arrangement preferably comprises the dispenser head, and wherein the dispenser head is configured to transfer the cosmetic composition from the mixing area to the dispenser head so as to dispense the cosmetic composition upon actuation. To this end it is conceivable that the dispenser head is configured analogous to a dispenser head as it is known in the art. That is, the dispenser head according to the invention can be configured displaceably with respect to the housing of the fluid dispenser, and wherein a displacement of the dispenser head towards the housing, for example by pressing the dispenser head downwards, results in a transfer of the cosmetic composition, in particular in a dispensing of the cosmetic composition from the dispenser head.

It is furthermore preferred that the dispensing arrangement comprises an actuation arrangement that operates in stages and which is configured to provide a feedback to a user. If a user then actuates a first stage of the actuation arrangement, the dispensing arrangement actuates the first dosing arrangement and/or the second dosing arrangement in a first step, whereby the dose of the first fluid and/or the dose of the second fluid are generated. After a preferably preset amount of time, which is indicative of a presence of the doses of the first fluid and/or of the second fluid in the mixing area, the actuation arrangement provides a feedback to the user. A feedback could be provided in the form of an optical signal such as a blinking light or a tactile signal such as a vibration or a sound signal such as a beep, for example. In response to the feedback the user can then actuate a second stage of the actuation arrangement, whereupon the dispensing arrangement transfers the cosmetic composition from the mixing area to the dispenser head in a second step. The actuation arrangement could be provided in the form of an operating element such as a button or switch which can be pressed or touched by a user, and which button or switch is in connection, preferably in electrical connection, with the first dosing arrangement and/or the second dosing arrangement. Said button or switch could be configured such, that a first pressing or touching by a user results in the actuation of the dosing arrangement(s), and that a further pressing or touching results in the transfer of the cosmetic composition from the mixing area to the dispenser head. However, other embodiments are likewise conceivable. For example, an operating element such as a button or switch could be arranged on the dispenser head, and wherein the dispenser head is actuatable. An actuatable dispenser head could be a dispenser head as it is known in the art, e.g. a dispenser head that can be pressed down towards the housing of the fluid dispenser. In this case, in a first step, the user actuates the first and/or second dosing arrangements by pressing or touching the button or switch, whereupon the dose of the first fluid and/or the dose of the second fluid is generated. Upon receipt of the feedback, the user can then press the dispenser head down, whereby the cosmetic composition is transferred from the mixing area to the dispenser head. In again another embodiment it is conceivable that the dispenser head itself is configured such, that it can adopt at least two stages. For example, it could be configured to be pressed downwards into a first stage, wherein the first and/or second dosing arrangement is/are actuated, and it could be further configured to be pressed downwards from said first stage into a second stage, wherein the cosmetic composition is transferred from the mixing area to the dispenser head for dispensing.

It is furthermore conceivable that the actuation arrangement comprises a sensing element that can sense a state of the mixing area and that can provide the feedback to the user in dependence of the sensed state of the mixing area. A state of the mixing area could correspond to the presence or absence of first fluid and/or second fluid in the mixing area. To this end it is therefore furthermore preferred that the sensing element is in connection with the mixing area. For example, the sensing element could be a pressure sensor that is connected to the mixing area, which pressure sensor detects a pressure exerted by fluid being present in the mixing area. If said sensed pressure equals a pre-set pressure value, the pressure sensor can send a feedback signal to the user. If a user actuates the first stage of the actuation arrangement such as pressing or touching the operating element in the form of the button or switch, the dispensing arrangement actuates the first dosing arrangement and/or the second dosing arrangement in a first step, whereby the dose of the first fluid and/or the dose of the second fluid are generated. Once that the dose or the doses of the first fluid and/or of the second fluid are present in the mixing area, the sensing element will sense this presence and provide a feedback to the user. A feedback could be again provided in the form of an optical signal such as a blinking light or a tactile signal such as a vibration or a sound signal such as a beep, for example. In response to the feedback the user can then actuate a second stage of the operating element such as further pressing or touching the button or switch, whereupon the dispensing arrangement transfers the cosmetic composition that has been generated in the first step from the mixing area to the dispenser head in a second step.

The dispensing arrangement preferably comprises the mixing area. That is to say, the mixing area is preferably arranged within the dispensing arrangement.

It is furthermore preferred that the dispensing arrangement comprises at least part of the second dosing arrangement. Alternatively, it is likewise preferred that the dispensing arrangement and the second dosing arrangement are configured separately from one another and are in fluid connection with one another, preferably via a fluid channel. In any case it is preferred when the second dosing arrangement is at least partially provided within a fluid communication being established between the second receptacle and the mixing area. However, it is also conceivable that the second dosing arrangement is provided entirely within the fluid communication that is established between the second receptacle and the mixing area.

Moreover, it is conceivable that the dispensing arrangement comprises at least part of the first dosing arrangement. However, it is preferred that the dispensing arrangement and the first dosing arrangement are configured separately from one another and are in fluid communication with one another, preferably via a fluid channel. In fact, the first dosing arrangement can be at least partially provided within a fluid communication being established between the first receptacle and the mixing area. However, it is also conceivable that the first dosing arrangement is provided entirely within the fluid communication that is established between the first receptacle and the mixing area.

The first dosing arrangement and/or the second dosing arrangement can be a pump, preferably a micropump or a piston pump, and/or a venturi nozzle.

The micropump can be a mechanical micropump or a non-mechanical micropump as it is known in the art. Examples of a mechanical micropump encompass diaphragm micropumps such as piezoelectric micropumps and peristaltic micropumps. Non-mechanical micropumps encompass valveless micropumps, capillary pumps, and chemically powered pumps, for example. The piston pump preferably corresponds to a piston pump as it is known in the art, i.e. a type of a displacement pump. The venturi nozzle likewise preferably corresponds to a venturi nozzle as it is known in the art, i.e. a pipe or tube which effectuates a venturi effect, i.e. a reduction in fluid pressure when the first fluid and/or the second fluid flows through the pipe or tube. Hence, the first and second dosing elements can correspond to commercially available components.

The first dosing arrangement, in particular the said pump, is preferably configured to prepare a dose of the first fluid in the range of between about 1 microliter to 200 microliter, preferably in the range of between about 5 to 30 microliter, more preferably in the range of about 5 microliter to microliter 20 microliter. Additionally or alternatively, the first dosing arrangement, in particular said pump, is preferably configured to prepare a dose of the first fluid being less than 40 microliter, preferably less than 30 microliter, particularly preferably less than 20 microliter. Likewise, the second dosing arrangement, in particular the said pump, is configured to prepare a dose of the second fluid in the range of between about 1 microliter to 200 microliter, preferably in the range of between about 5 to 30 microliter, more preferably in the range of about 5 microliter to microliter 20 microliter. Additionally or alternatively, the second dosing arrangement, in particular said pump, is preferably configured to prepare a dose of the second fluid being less than 40 microliter, preferably less than 30 microliter, particularly preferably less than 20 microliter.

It is furthermore preferred that the first dosing arrangement is adjustable such that varying doses of the first fluid can be generated. It is likewise preferred that the second dosing arrangement is adjustable such that varying doses of the second fluid can be generated. It is furthermore preferred that the first dosing arrangement and the second dosing arrangement are set and/or adjustable in such a way, that a dose of the first fluid is smaller than a dose of the second fluid, or vice versa. Namely, as the cosmetic composition preferably corresponds to a perfume that is formed by mixing a first fluid comprising one or more fragrant essential oils, one or more aroma compounds, or mixtures thereof with a second fluid comprising an aqueous solution, preferably water, see also further below, it is preferred that the dose of the first fluid is smaller than the dose of the second fluid. Against this background it is therefore preferred if the first dosing arrangement is configured or set such that a dose of the first fluid being in the range of about 10 microliter to 20 microliter is generated, and that the second dosing arrangement is configured or set such that a dose of the second fluid being in the range of 60 to 70 microliter is generated.

Moreover, the first dosing arrangement can be configured to generate the dose of the first fluid as droplets of the first fluid. Additionally or alternatively the second dosing arrangement can be configured to generate the dose of the second fluid as droplets of the second fluid.

Droplets of the first fluid and of the second fluid can be generated depending on the kind of dosing arrangements and in particular depending on the operation conditions applied to the dosing arrangements. For example, if the dosing arrangements correspond to a micropump, an opening time or an oscillation frequency of the micropump can result in the formation of droplets of fluid. However, it should be noted that the kind of dosing arrangements and in particular the operation conditions applied to the dosing arrangements can likewise result in a continuous flow of fluid through the dosing arrangements. For example, it is conceivable that the first dosing arrangement and the second dosing arrangement in each case correspond to a piezoelectric micropump, wherein the first dosing arrangement is driven with a first oscillation frequency being able to generate droplets of first fluid, whereas the second dosing arrangement is driven with a second oscillation frequency being higher than the first oscillation frequency such that a continuous flow of second fluid is obtained.

The first dosing arrangement can be provided in the housing or on the first reservoir or in the first reservoir or in the dispenser head. Additionally or alternatively the second dosing arrangement can be provided in the housing or on the second reservoir or in the second reservoir or in the dispenser head.

Hence, it is conceivable to provide the first dosing arrangement and/or the second dosing arrangement as an integral component of the fluid dispenser. For example, the dosing arrangements could be arranged within the dispenser head or the housing, preferably within a fluid channel as mentioned above or at an interface between the first receptacle and/or the second receptacle and said fluid channels. However, it is likewise conceivable that the first dosing arrangement and/or the second dosing arrangement in each case constitute a component being removable from the fluid dispenser. For example, the first dosing arrangement and/or the second dosing arrangement could be arranged on or in the first reservoir and the second reservoir, respectively. As will be explained in greater detail below, the first reservoir and/or the second reservoir can be provided in the form of a container or capsule which is removably connectable to the fluid dispenser. Hence, it is conceivable that said container or capsule comprises a dosing arrangement which enables a dispensing of the fluid comprised within the container or capsule from the container or capsule as a dose, and wherein said dosing arrangements are removable from the fluid dispenser by removing the container or capsule from the fluid dispenser.

The mixing area can be provided within a mixing chamber, and wherein the first receptacle, the second receptacle and the dispenser head are in fluid communication with the mixing chamber.

That is, the fluid dispenser can comprise a mixing chamber which delimits or encompasses the mixing area, and wherein said mixing chamber is in fluid communication, preferably in fluid connection via respective fluid channels, with the first and second receptacles and the dispenser head.

The mixing chamber can be arranged within the housing or within the dispenser head.

For example, the mixing chamber could be formed within the housing or could be arranged within a recess formed within the housing or the dispenser head, respectively. That is, the mixing chamber could be provided as integral part of the housing or the dispenser head, wherein the housing together with the mixing chamber or the dispenser head together with the mixing chamber are configured as a single-piece element, respectively. Alternatively, the mixing chamber and the housing or the mixing chamber and the dispenser head can be provided as separate and individual parts, wherein the mixing chamber is insertable into the housing or the dispenser head, respectively.

If the mixing chamber comprises the mixing area the first dosing arrangement can be arranged at least partially or entirely within the fluid communication that is established between the first receptacle and the mixing chamber. Similarly, the second dosing arrangement can be arranged at least partially or entirely within the fluid communication that is established between the second receptacle and the mixing chamber.

The mixing chamber can comprise a rigid material or a flexible material and/or a compressible material. Conceivable rigid materials are plastics, preferably thermosetting polymers, or glass or metals such as aluminium or combinations thereof. Conceivable flexible and/or compressible materials are plastics, preferably thermoplastics such as polyethylene terephthalate (PET), polyethylene (PE) or polypropylene (PP) or combinations therefor. It is furthermore conceivable that two or more of these materials are provided in a layered form.

A mixing chamber comprising a flexible and/or compressible material enables a mixing chamber that has a variable volume. For example, if first fluid and/or second fluid enters the mixing chamber, a first volume of the mixing chamber can increase and adopt a second volume that is larger than the first volume. If the cosmetic composition is removed from the mixing chamber, the volume of the mixing chamber can reduce again. In this sense, the mixing chamber can be seen as a flexible and/or compressible bag or pouch.

In a first variant, the dispensing arrangement can comprise a dispensing chamber and an actuating element that is arranged within the dispensing chamber, wherein the dispensing chamber is in fluid communication with the mixing chamber and the dispenser head. The dispensing arrangement is preferably configured such, that the cosmetic composition is transferable from the mixing chamber to the dispenser head upon an actuation of the actuating element. Since the mixing area, in particular the mixing chamber, is in fluid communication with the dispensing arrangement, an actuation of the dispensing arrangement results in a transfer of the cosmetic composition from the mixing area, in particular from the mixing chamber, to the dispenser head.

The actuating element can be displaceably mounted within the dispensing chamber, and the dispenser head can be spring-loaded and displaceably arranged on the housing. In this case, the dispensing arrangement is preferably configured such, that the actuating element is movable from an initial position to a final position during a flow of first fluid and/or of second fluid into the mixing chamber. In the initial position of the actuating element, the actuating element preferably rests on a bottom wall of the dispensing chamber. In the final position of the actuating element, the actuating element is preferably spaced apart from said bottom wall. Preferably, the dispenser head is likewise configured such, that it is movable from an initial position into a final position. In the initial position of the dispenser head, the dispenser head is preferably spaced apart from the housing by a first distance as a result of its spring-loaded design. In a second position of the dispenser head, the dispenser head has been moved against a spring-force and towards the housing such that it is spaced apart from the housing by a second distance being smaller than the first distance. It is furthermore preferred in this case that the actuating element and the dispenser head can be operatively connected with one another, such that the movement of the dispenser head from its initial position into its final position results in a movement of the actuating element from its final position into its initial position, whereby the cosmetic composition being present in the mixing chamber is transferred to the dispenser head. The actuating element preferably is a piston that is displaceably arranged within the dispensing chamber. Since a displacement of the dispenser head results in a transfer of the cosmetic composition from the mixing chamber to the dispenser head, it can be said that the dispenser head forms part of the actuation arrangement mentioned above and therefore of the dispensing arrangement.

Alternatively, it is conceivable that the actuating element is spring-loaded and displaceably mounted within the dispensing chamber. The actuating element preferably is a spring-loaded piston. Different arrangements of the spring on the piston are conceivable. For example, the spring could be arranged before the piston or after the piston with respect to a pressing direction extending from the dispenser head towards the housing. In other words, the spring could be arranged above the piston or below the piston when the fluid dispenser is seen in its installation position. In any case, it is preferred that the actuating element is movable from an initial position into a final position. However, in contrast to the just-described case, it is preferred here that the actuating element is arranged spaced apart from a bottom wall of the dispensing chamber in an initial position as a result of its spring-loaded design, and wherein the first fluid and/or the second fluid can flow into the mixing chamber while the actuating element is in its spaced-apart position. The cosmetic composition being present in the mixing chamber can be transferred from the mixing chamber to the dispenser head during a movement of the actuating element against its spring-force and towards the bottom wall of the dispensing chamber into its final position. An actuation of the actuating element is caused by an actuation of the dispensing arrangement. For the sake of completeness it is mentioned once more that an actuation of the dispensing arrangement preferably takes place by actuating its actuation arrangement. In this case, it is preferred that said actuation arrangement comprises, inter alia, an actuatable dispenser head that can be pressed down towards the housing of the fluid dispenser, and wherein said movement is transferred to the actuating element in the form of the spring-loaded piston.

The dispenser head is preferably in fluid connection with the mixing area, preferably via a fluid channel, particularly preferably via a fluid channel that extends through the actuating element or between the actuating element and an inner wall of the dispensing chamber.

That is to say, a transfer of the cosmetic composition from the mixing area to the dispenser head can be achieved in various ways. For example, it is conceivable that the mixing area, in particular the mixing chamber, and the dispenser head are in fluid communication with one another via a fluid channel. Said fluid channel can connect an outlet opening being provided in the mixing chamber with an inlet opening being provided in the dispenser head. Moreover, in the event that the dispensing arrangement comprises a dispensing chamber with an actuating element being arranged therein, a fluid channel can be formed between the actuating element and an inner wall of the dispensing chamber. To this end it is preferred that a cross-section of the dispensing chamber is larger than a cross-section of the actuating element. Upon actuation of the actuating element, the cosmetic composition can then flow through the fluid channel that is formed between the inner wall of the dispensing chamber and the actuating element. Alternatively, it is likewise conceivable that a fluid channel is formed within the actuating element and which extends through the actuating element such that the cosmetic composition can be transferred from the mixing chamber to the dispenser head through the actuating element.

The dispensing chamber can correspond to the mixing chamber. That is, the dispensing chamber and the mixing chamber can be provided by means of the same component. Alternatively, the dispensing chamber and the mixing chamber can be configured separately from one another and can be in fluid connection with one another, preferably via a fluid channel. In the latter case the dispensing chamber is in fluid communication with the second receptacle and the mixing chamber such that the second fluid is transferable from the second reservoir to the mixing chamber via the dispensing chamber. Moreover, it is conceivable that the dispensing arrangement is configured such, that the second fluid is transferable from the second reservoir into the mixing chamber after the actuation of the actuating element. Alternatively, it is conceivable that the fluid dispenser further comprises at least a first balancing arrangement which enables a fluid communication between the mixing chamber and an exterior of the mixing chamber, and wherein the first balancing arrangement is configured such, that a balancing fluid is transferable from the exterior of the mixing chamber into the mixing chamber after the actuation of the actuating element. The balancing fluid preferably corresponds to air, particularly preferably to ambient air. These different situations shall be explained by means of the following examples.

In fact, and as has already been mentioned earlier, the dispensing arrangement can be configured such, that an actuation of the first dosing arrangement and of the second dosing arrangement in order to generate the dose of the first fluid and the dose of the second fluid, and thus the generation of the cosmetic composition in the mixing area, occurs in a first step and that the transfer of the cosmetic composition from the mixing area to the dispenser head occurs in a second step. It has also already been mentioned that the dispensing arrangement comprises an actuation arrangement that operates in stages. Hence, as a first example it is conceivable that the first dosing arrangement corresponds to a micropump that is arranged within a fluid channel that connects the first receptacle with the mixing chamber, and that the second dosing arrangement comprises a spring-loaded piston that is displaceably mounted within the dispensing chamber. To this end the spring-loaded piston of the second dosing arrangement constitutes the actuating element of the dispensing arrangement. That is, the dispensing arrangement comprises at least part of the second dosing arrangement. If a user actuates the dispensing arrangement, for example by touching a button or switch, the actuated dispensing arrangement will actuate the first dosing arrangement such that a dose of first fluid is transferred into the mixing chamber. Since a dose of the second fluid is already present in the mixing chamber because of an actuation of the second dosing arrangement during a previous dispensing cycle, the cosmetic composition is thereby generated. If the user then further actuates the dispensing arrangement by pushing the spring-loaded piston and possibly upon receipt of a feedback signal from the actuation arrangement, the actuating element transfers the cosmetic composition from the mixing chamber to the dispensing head. By using a preloaded or pretensioned actuating element such as the spring-loaded piston, the force exerted by the spring onto the piston will automatically, i.e. without any external impact, move the piston from a compressed state after an actuation of the actuating element into an uncompressed state. Such a movement automatically. i.e. without any external impact, pulls second fluid from the second reservoir into the mixing chamber as a result of capillary forces or a pressure difference caused by the moving actuating element or the like. Consequently, in a rest state, i.e. after an actuation but before any further actuation of the dispensing arrangement, second fluid will be present in the mixing chamber. Upon a further actuation of the dispensing arrangement, the dispensing arrangement actuates the first dosing arrangement, for example by sending the first dosing element trigger signal to the first dosing arrangement, wherein droplets of the first fluid are added to the second fluid that is already present in the mixing chamber. Thereby, a further cosmetic composition is generated. A fluid dispenser comprising the above-mentioned first balancing arrangement can be used if a permanent presence of second fluid within the mixing chamber is not desired. Hence, as a second example it is conceivable that the first dosing arrangement and the second dosing arrangement in each case correspond to a micropump, wherein one micropump is arranged within a fluid channel that connects the first receptacle with the mixing chamber, and the other micropump is arranged within a fluid channel that connects the second receptacle with the mixing chamber. As in the first example, the dispensing arrangement can comprise a dispensing chamber within which a spring-loaded piston is movably arranged. The dispensing chamber corresponds to the mixing chamber. The first balancing arrangement preferably corresponds to a valve such as a mechanical valve comprising a ball and which enables a fluid communication between the mixing chamber (the dispensing chamber) and an exterior of the mixing chamber (dispensing chamber), for example a part of the housing which houses the mixing chamber (dispensing chamber). Said part of the housing could be another receptacle within which the mixing chamber (dispensing chamber) is arranged. The exterior of the mixing chamber (dispensing chamber), such as said part of the housing, preferably comprises a balancing fluid such as ambient air. In this case, the fluid communication established between the mixing chamber (dispensing chamber) and the exterior allows a transfer of the balancing fluid from the exterior of the mixing chamber (dispensing chamber) into the mixing chamber (dispensing chamber) as well as from within the mixing chamber (dispensing chamber) into the exterior of the mixing chamber (dispensing chamber) via the first balancing arrangement. In a rest state, i.e. before any further actuation of the fluid dispenser, balancing fluid is present in the mixing chamber (dispensing chamber). This is in contrast to the former situation described above, wherein second fluid is present in the mixing chamber (dispensing chamber) in the rest state. Upon a first actuation of the dispensing arrangement and thus an actuation of the dosing arrangements, the first fluid and the second fluid are allowed to flow into the mixing chamber (dispensing chamber), whereby the cosmetic composition is generated. Upon a second actuation of the dispensing arrangement, wherein the user pushes the spring-loaded piston, said cosmetic composition is transferred from the mixing chamber to the dispenser head. After said second actuation the spring force exerted by the spring onto the piston will move the piston back into its uncompressed state. However, and unlike in the first example, this movement will pull balancing fluid from the exterior of the mixing chamber (dispensing chamber) into the interior of the mixing chamber (dispensing chamber). That is to say, in this latter case the mixing chamber (dispensing) is filled with the first fluid as well as the second fluid on demand. Although the above examples concern in each case a fluid dispenser, wherein the mixing chamber corresponds to the dispensing chamber, it should be noted that they likewise apply to the situation where the mixing chamber and the dispensing chamber correspond to two different components that are in connection with one another.

In a second variant the dispensing arrangement can comprise at least one pressure assembly that is configured to exert a pressure onto the mixing chamber upon actuation, whereby the cosmetic composition is transferable from the mixing chamber to the dispenser head.

The pressure assembly can comprise a pressure element such as a fluid, at least a first pressure chamber and a second pressure chamber which are in fluid communication with one another preferably via at least a second balancing arrangement. The second balancing element preferably corresponds to a pump. The mixing chamber is preferably arranged within the second pressure chamber, and the pressure assembly is configured such, that at least part of the pressure element is transferred from the first pressure chamber into the second pressure chamber upon actuation of the pressure assembly, whereby the cosmetic composition is transferable from the mixing chamber to the dispenser head. It is furthermore preferred that the second pressure assembly is configured such, that the pressure element is transferred from the second pressure chamber back into the first pressure chamber after the cosmetic composition has been transferred from the mixing chamber to the dispenser head. An actuation of the pressure assembly preferably takes place via the actuation arrangement of the dispensing arrangement, which can comprise here again a button or switch or an actuatable dispenser head or combinations thereof, see above.

In a third variant, the dispensing arrangement can comprise a dispensing chamber and an actuating element that is displaceably arranged within the dispensing chamber, wherein the dispensing chamber is in fluid communication with the second receptacle or encompasses the second receptacle, wherein the dispensing chamber is further in fluid communication with the first receptacle, the dispenser head, and the venturi nozzle.

As has been mentioned initially, the first dosing arrangement and/or the second dosing arrangement can be provided by means of a venturi nozzle. That is, the dose of the first fluid and/or of the second fluid can be generated by means of the venturi nozzle.

It is preferred that the venturi nozzle comprises the mixing area. To this end it is conceivable that the first receptacle is in fluid communication, preferably in fluid connection via a fluid channel, with the venturi nozzle. In this case the mixing area is provided within the venturi nozzle in a region where said fluid channel connects to or merges into the venturi nozzle. It is furthermore preferred that the second receptacle is in fluid communication, preferably in fluid connection via a fluid channel, with the dispensing chamber. Alternatively, it is conceivable that the second receptacle is encompassed by the dispensing chamber.

Moreover, it is conceivable that the actuating element is configured such that a flow of second fluid from the second reservoir into the mixing area is generated upon an actuation of the actuating element, whereby the cosmetic composition is generated in the mixing area. The actuating element preferably is a piston, particularly preferably a spring-loaded piston that can be actuated by a user. Hence, if a user actuates the dispensing arrangement by pulling the actuating element along a proximal direction such, that a volume within the dispensing chamber that is delimited by the actuating is increased, a dose of second fluid is pulled from the second reservoir into the dispensing chamber in a first step. If the user then further actuates the dispensing arrangement by pushing the actuating element along a distal direction running opposite to the proximal direction, the second fluid is dispensed from the dispensing chamber towards the dispenser head via the venturi nozzle. During the flow of second fluid through the venturi nozzle, a dose of first fluid is pulled from the first receptacle into the venturi nozzle as a result of the venturi effect. Thereby, the cosmetic composition is generated within the venturi nozzle. During said pushing movement along the distal direction the cosmetic composition is readily dispensed from the dispenser head.

The fluid dispenser can further comprise a droplet generator, the droplet generator being in fluid communication with the dispenser head, the first receptacle and the second receptacle and being configured to generate droplets of the first fluid when the first fluid flows in said droplet generator. The droplet generator can be identified with a first dosing arrangement and/or a second dosing arrangement as described above. The droplet generator can comprise the mixing area or the droplet generator can be in fluid communication with the mixing area. In the former case, the mixing area is a component of the droplet generator and preferably arranged within the droplet generator. In the latter case, the mixing area is a separate component and is arranged outside of the droplet generator. The droplet generator according to this latter case is preferably configured to deliver a dose of droplets of the first fluid to the second fluid.

Hence, in a first aspect, the mixing area, in particular the droplet generator, can be in fluid communication with the first receptacle and the second receptacle via a first fluid channel and a second fluid channel, respectively, and wherein the first fluid channel merges into the second fluid channel within the mixing area, in particular within the droplet generator, such that droplets of the first fluid being dispersed in the second fluid, and thereby the cosmetic product, are generated. The droplet generator according to the first aspect preferably is a microfluidic device.

In a second aspect, the first receptacle and the droplet generator can be in fluid communication via a first fluid channel, wherein the second receptacle and the droplet generator are in fluid communication via a second fluid channel, and wherein the droplets of the first fluid generated in the droplet generator are dispersed from the droplet generator into the second fluid flowing in the second fluid channel, whereby the cosmetic composition is generated. The droplet generator according to the second aspect preferably comprises a piezoelectric element, and wherein the droplets of the first fluid are generated in the droplet generator upon activation of the piezoelectric element.

The fluid dispenser can further comprise at least one selection device being in communication with at least one of: the first receptacle, the first reservoir when in connection with the first receptacle, the second receptacle, the second reservoir when in connection with the second receptacle, the first dosing arrangement, the second dosing arrangement, and the droplet generator such that a selected dose of the first fluid is dispensed from the first receptacle and/or a selected dose of the first fluid is dispensed from the first reservoir and/or a selected dose of the second fluid is dispensed from the second receptacle and/or a selected dose of the second fluid is dispensed from the second reservoir and/or a selected dose of the first fluid is generated by the first dosing arrangement and/or a selected dose of the second fluid is generated by the second dosing arrangement and/or a selected dose of droplets of the first fluid is generated in the droplet generator. The selection device is preferably adjustable between at least a first selection mode and a second selection mode.

It is preferred that the first selection mode differs from the second selection mode for example such that less droplets per unit time are generated when the selection device is set to the first selection mode than when the selection device is set to the second selection mode. The same applies to the dispensing of the first and/or second fluids from the first and/or second receptacles and from the first and/or second reservoirs if said reservoirs are in connection with the receptacles. Moreover, it is conceivable that the selection device is adjustable between more than two selection modes.

Hence, the selection device allows adjusting the constitution of the cosmetic composition. For example, the concentration of the first and second fluids can be varied in that more or less first fluid is mixed with the second fluid. This adjustment or variation can again be realized by a user on demand and in the moment of using the dispenser.

It is preferred that the first fluid and the second fluid are essentially immiscible with each other. Essentially immiscible means that the first fluid can be dispersed in the second fluid, or vice versa. Moreover, it is conceivable that an emulsion is formed by the first and second fluids. To this end it is conceivable that a mixing element is provided in the region of the mixing area which assists or enables the generation of an emulsion by actively mixing the first and second fluids with each other.

The first fluid is preferably selected from the group consisting of one or more fragrant essential oils, one or more aroma compounds, or mixtures thereof, and/or the second fluid preferably corresponds to an aqueous solution, preferably water.

The first fluid is preferably provided in the form of highly concentrated one or more aroma compounds and/or one or more fragrant essential oils, i.e. the first fluid is preferably provided as a pure one or more aroma compounds and/or as a pure one or more fragrant essential oils. The second fluid is preferably water.

In other words, the fluid dispenser enables the generation of a cosmetic composition being free of alcohol and thus being very suitable for skin-sensitive people or children. However, it is also conceivable that the second fluid is provided by means of an aqueous solution such as a water-ethanol-solution.

The first fluid can be seen as a fragrance and the second fluid can be seen as the carrier of said fragrance. By adjusting the selection device accordingly, a user can generate a cosmetic composition, in particular a perfume, comprising for example.
- up to 40% by volume of the fragrance and up to 60% by volume of the carrier, resulting in a so-called extrait parfum,
- about 10 to 14% by volume of the fragrance and about 86 to 90% by volume of the carrier, resulting in a so-called eau de parfum,
- about 6 to 9% by volume of the fragrance and about 91 to 94% by volume of the carrier, resulting in a so-called eau de toilette, etc.

The cosmetic product is preferably essentially free from additives such as stabilizers and/or preservatives and/or antioxidants and/or emulsifiers and/or surfactants.

By mixing the components of the cosmetic composition essentially immediately before the cosmetic composition is dispensed additives used for the stabilization of the dispersion, for example, can be dispensed with.

The first reservoir can be provided in the form of a first container that is removably connectable to the first receptacle, said first container preferably having the shape of a capsule. In addition or alternatively the second reservoir can be provided in the form of a second container that is removably connectable to the second receptacle, said second container preferably having the shape of a capsule, or the second reservoir can be connected to the second receptacle and can be an integral part of the housing. In the former case it is conceivable to provide the second reservoir in the form of a second container which constitutes a lower part of the fluid dispenser itself. To this end it is preferred that said second container comprises a connection element that allows its preferably removable connection with an upper part of the fluid dispenser, in particular with a corresponding connection element provided on said upper part of the fluid dispenser. For example, the lower part of the fluid dispenser could comprise an external thread that can establish a screw connection with an inner thread provided on the upper part of the fluid dispenser.

Hence, on the one hand side it is conceivable to provide the first reservoir in the form of a container, in particular in the form of a capsule that is prefilled with the first fluid, particularly preferably with a first fluid consisting of a highly concentrated one or more aroma compounds and/or one or more fragrant essential oils as mentioned above. Also the second reservoir can be provided in the form of a container, in particular in the form of a capsule that is prefilled with the second fluid, particularly preferably with a second fluid not being water such as an alcohol-containing aqueous solution for example. If the first and/or second reservoir is empty or if the user wishes the generation of a cosmetic composition comprising different constituents the user can simply remove and exchange the first and/or second reservoir. To this end it is also conceivable that the second reservoir is designed so as to be fillable with the second fluid by a user. In this case the user can simply disconnect the second reservoir from the fluid dispenser, fill the second reservoir with e.g. water, and then reconnected the filled second reservoir to the fluid dispenser. On the other hand it is however also conceivable that the second receptacle and the second reservoir are provided as a single-piece element, wherein the second receptacle could be seen as a casing that at least partially encases the second reservoir. That is, it is conceivable to provide the second reservoir as an integral part of the housing. In order to allow a filling of the second reservoir with the second fluid or a removal of the second fluid from the second reservoir the second reservoir preferably comprises one or more openings through which the second fluid can be filled into the second reservoir and/or through which the second fluid can be drained off from the second reservoir. Many advantages are associated with these designs. For example, the fluid dispenser does not have to be disposed once the fluids are used up but can simply be refilled with new fluids and the fluid dispenser can thus be reused. In addition, a user can use different first and/or second fluid compositions such that different cosmetic compositions are generated by means of the same fluid dispenser. Furthermore, a user can choose—according to different situations—among several removable second containers defining different volumes: For example a standard one when at home and a smaller one when travelling, while both of them are connectable, for example insertable into the second receptacle.

The first receptacle and/or the second receptacle can be provided in the form of recesses and/or openings in the housing into which the first reservoir and/or the second reservoir can be removably and partially or fully inserted. The reservoirs can then be held or retained in the recesses without any connection elements, for example by means of a form closure and/or a frictional connection only. It is however likewise conceivable to provide one or both of these receptacles with connection elements that allow a connection with corresponding connection elements provided on the first and second reservoirs. For example, the first and/or second receptacle and the first and/or second reservoir could be provided with corresponding screw threads such that the first and/or second reservoir can be connected to the first and/or second receptacle by means of a screw connection. Obviously the connection elements are not restricted to threaded connection elements but any sort of connection elements configured to establish a preferably releasable connection between a receptacle and a reservoir are conceivable. These connections are well-known to the skilled person and include, among others, snap-on or latching connections, for example.

The fluid dispenser preferably further comprises at least one activation device and/or an actuation arrangement. The activation device can be configured to transmit an activation signal to at least one of: the first receptacle, the first reservoir when in connection with the first receptacle, the second receptacle, the second reservoir when in connection with the second receptacle, the droplet generator, and the dispenser head such that a release of the first fluid from the first receptacle and/or a release of the first fluid from the first reservoir and/or a release of the second fluid from the second receptacle and/or a release of the second fluid from the second reservoir and/or a release of droplets of the first fluid from the droplet generator and/or a dispensing of the cosmetic composition from the fluid dispenser is enabled. Hence, the activation device enables, upon activation, the release of the fluids, the mixing of the fluids, and the dispensing of the cosmetic composition, respectively. The cosmetic composition is thus freshly and only generated when a user intends to use it. The actuation arrangement can be configured to actuate at least one of the first dosing arrangement, the second dosing arrangement, the pressure assembly such that a generation of droplets of the first fluid by the first dosing arrangement and/or a generation of droplets of the second fluid by the second dosing arrangement and/or a transfer of the cosmetic composition from the mixing chamber to the dispenser head by the pressure assembly is enabled The activation device preferably comprises or is operatively connected with the actuation arrangement of the dispensing arrangement. In this case an activation of the activation device results in an actuation of the actuation arrangement, whereby the first and/or second dosing arrangements are actuated and the cosmetic composition is transferred from the mixing area to the dispenser head.

The fluid dispenser can further comprise at least one power supply configured to supply power to at least one of: the activation device, the first receptacle, the first reservoir when in connection with the first receptacle, the second receptacle, the second reservoir when in connection with the second receptacle, the actuation arrangement, the dispensing arrangement, the first dosing arrangement, the second dosing arrangement, the pressure assembly, the droplet generator, and the dispenser head. The at least one power supply can be provided in the form of an electrical or a mechanical power supply. For example, the power supply could be a battery or a solar cell adapted to supply electrical power. On the other hand the power supply could correspond to a mechanical device which is operatively connected with the said components and which, upon activation, activates the said components. Alternatively, the mechanical device could also be configured such that mechanical energy is transferred into electrical energy, and wherein said electrical energy is then supplied to the said components.

The fluid dispenser can further comprise at least one level indicator being configured to indicate the amount of the first fluid in the first reservoir and/or being configured to indicate the amount of second fluid in the second receptacle and/or being configured to indicate the amount of first fluid and/or second fluid in the mixing chamber and/or being configured to indicate the amount of cosmetic composition in the mixing chamber. The level indicator informs the user about the filling level of the first and second reservoirs and timely indicates that the reservoirs have to be replaced or refilled, respectively.

The housing can be comprised of at least a first housing part and a second housing part, wherein the first housing part and the second housing part of the housing are designed to be rotatable with respect to one another, and wherein the first receptacle is arranged in the first housing part of the housing and the second receptacle is arranged in the second housing part of the housing.

As already mentioned initially, the fluid dispenser can comprise two or more first and/or second receptacles that are in each case connectable to a first and/or second reservoir. For example, the fluid dispenser can comprise two first receptacles into which two first reservoirs comprising different first fluids are inserted and one second receptacle into which a second fluid is inserted. The different first fluids could differ in the particular fragrant essential oils or aroma compounds they are made of. In a first position the mixing area is in fluid communication with the second receptacle and the second fluid comprised therein and with one of the first receptacles and the first fluid comprised therein. If a user wishes to change the chemical composition of the cosmetic composition he can rotate the two housing parts against each other, whereby the mixing area enters into fluid communication with the other of the first receptacle and the first fluid comprised therein. In this second position a cosmetic composition is generated that differs from the cosmetic composition generated in the first position due to the different first fluid being used. To this end it is preferred that the fluid dispenser is configured such, that the housing parts can adopt an intermediate position. Said intermediate position is adopted between the first position and the second position and corresponds to a position in which no fluid communication is established between the mixing area and the first receptacles. If a user now activates the activation device, only the residual cosmetic composition comprised in the fluid dispenser is dispensed from the fluid dispenser. However, no new cosmetic composition is generated. This intermediate position can thus be seen as a cleaning position.

In a further aspect a method of producing a fluid dispenser, in particular a perfume dispenser, for dispensing a cosmetic composition, in particular a perfume, is provided. The fluid dispenser preferably is a fluid dispenser as described above. The method comprises the steps of:

Providing a housing;

Arranging a dispenser head being configured to dispense the cosmetic composition from the fluid dispenser on the housing;

Providing at least one first receptacle being connectable to at least one first reservoir comprising a first fluid in the housing;

Providing at least one second receptacle being connectable or connected to a second reservoir in the housing, the second reservoir being configured to receive a second fluid; and Providing a mixing area in the housing, the mixing area being in fluid communication with the dispenser head, the first receptacle and the second receptacle. The mixing area is configured such, that the cosmetic composition is generated when a dose of the first fluid is mixed with the second fluid within the mixing area.

In a further aspect a reservoir preferably in the form of a capsule for use in a fluid dispenser as described above is provided. The reservoir is fillable and/or filled with a fluid used in the generation of the cosmetic composition.

That is, said reservoir can be prefilled with the first fluid or with the second fluid. Moreover, it is conceivable that the capsule is additionally or alternatively configured so as to be fillable and/or refillable with the first fluid and/or the second fluid.

In a further aspect a use of a reservoir preferably in the form of capsule in a fluid dispenser as described above is provided. The reservoir is fillable and/or fillable with a fluid used in the generation of the cosmetic composition. Here, too, it is conceivable that said reservoir is prefilled with the first fluid or with the second fluid and/or that the capsule is configured so as to be fillable and/or refillable with the first fluid and/or the second fluid.

Said reservoirs can in each case be identified with the first reservoir being connectable to the first receptacle and/or with the second reservoir being connectable to the second receptacle provided in the fluid dispenser. Therefore, any explanations provided above with respect to the first reservoir and the second reservoir being connectable to the second receptacle likewise apply to the reservoirs according to these further aspects. For example, the reservoir can be configured so as to deliver a dose of the first fluid (the second fluid) to the mixing area. Additionally or alternatively the reservoir can be configured to communicate or be in communication with the selection device and/or with the activation device and/or with the power supply and/or with the level indicator. Moreover, the reservoir can comprise a connection element that is configured to establish a preferably releasable connection with a corresponding connection element provided on the first receptacle (second receptacle) of the fluid dispenser. Alternatively, it is conceivable that the geometrical dimensions of the reservoir is mutually corresponding to the geometrical dimensions of the first receptacle (the second receptacle) such that a form closure and/or a frictional connection is established between the reservoir and the first receptacle (second receptacle) when the reservoir is at least partially inserted into the first receptacle (second receptacle).

In order to allow the filling of first fluid (second fluid) into the reservoir or a removal of the first fluid (second fluid) from the reservoir the reservoir can be provided with one or more apertures through which the first fluid (second fluid) can enter or leave the reservoir. Said one or more apertures can furthermore be configured to establish a fluid communication between the reservoir and the first receptacle (second receptacle) such that fluid comprised in the reservoir can be dispensed into the mixing area of the fluid dispenser. However, it is likewise conceivable that the reservoir comprises other means configured to establish a fluid communication between the reservoir and the mixing area. Said other means can be other one or more apertures than the one or more apertures configured for filling/removing the fluid from the reservoir or a valve, for example.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 7a shows a perspective view of a capsule for use with the fluid dispenser in a closed position:

FIG. 7b shows a perspective view of the capsule according to FIG. 7a in an opened position:

FIG. 8a shows a partial sectional view of the capsule according to FIG. 7a with an actuation element according to a first aspect in the closed position;

FIG. 8b shows a partial sectional view of the capsule according to FIG. 7b with the actuation element in the opened position;

DESCRIPTION OF PREFERRED EMBODIMENTS

Figure 1A:
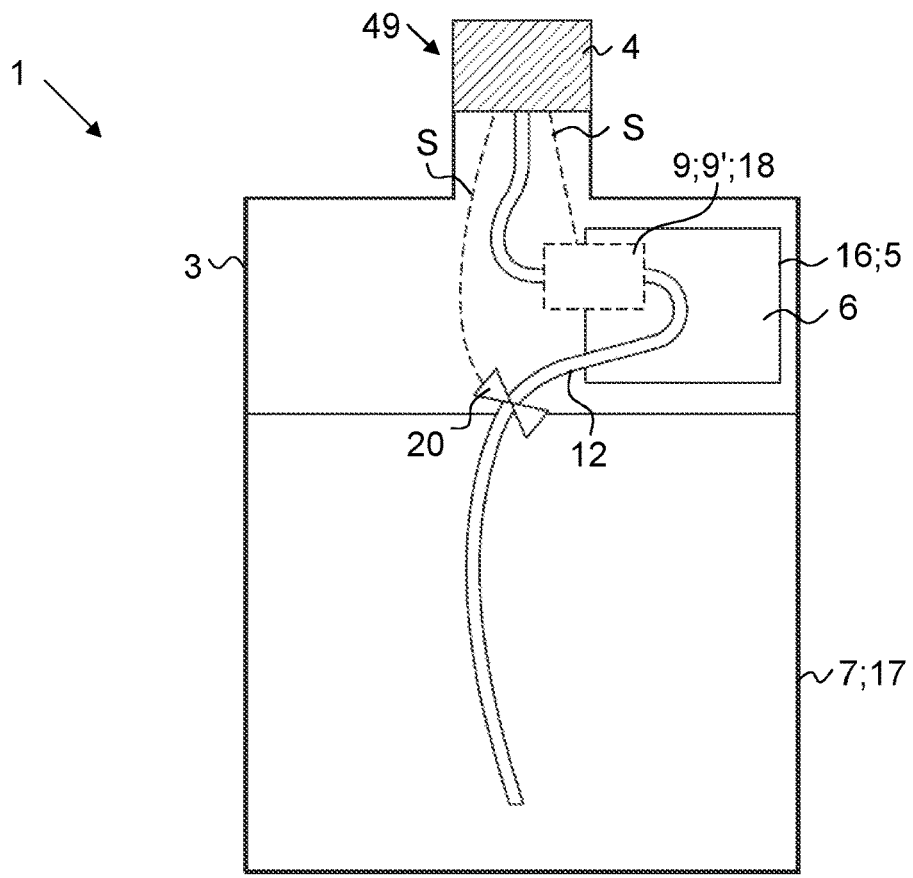
FIG. 1a shows a sectional view of a fluid dispenser according to a first aspect in a first position.

Several aspects of a fluid dispenser 1 for dispensing a cosmetic composition 2 such as a perfume dispenser for dispensing a perfume according to the invention are disclosed in FIGS. 1 to 18. The fluid dispensers 1 depicted in these figures have in common that they comprise in each case a housing 3, a dispenser head 4 being arranged on the housing 3, at least one first receptacle 16 being provided in the housing 3, and at least one second receptacle 17 being provided in the housing 3. The dispenser head 4 is configured to dispense the cosmetic composition 2 from the fluid dispenser 1. The first receptacle 16 is connectable to a first reservoir 5 comprising a first fluid 6, and the second receptacle 17 is connectable or connected to a second reservoir 7. The second reservoir 7 is configured to comprise a second fluid 8. The fluid dispensers 1 further comprise a mixing area 18 being in fluid communication with the dispenser head 4, the first receptacle 16 and the second receptacle 17. The mixing area 18 is configured such, that the cosmetic composition 2 is generated when a dose of the first fluid 6 is mixed with the second fluid 8 within the mixing area 18. As will be explained in detail in the following, the generation of the dose of the first fluid, and potentially also the generation of a dose of the second fluid, can be accomplished in several ways.

With reference to FIGS. 1a to 1d a fluid dispenser 1 is disclosed which comprises a dispenser head 4 and two receptacles 16, 17 provided in the housing 3. A first reservoir 5 having the form of an essential rectangular capsule and being filled with a first fluid 6 is accommodated completely within the first receptacle 16. To this end the first receptacle 16 has the shape of a recess extending from an outside of the housing 3 towards an inside of the housing 3 so as to allow a user to insert the first reservoir 5 comprising the first fluid 6 into the first receptacle 16 from the outside. The dimensions of the first receptacle 16 and the first reservoir 5 are such, that the first reservoir 5 is held within the first receptacle 16 by means of a form closure and/or a frictional connection only. The second receptacle 17 and the second reservoir 7 are provided as a single piece element, wherein the second receptacle 17 is designed as a casing that at least partially encases the second reservoir 7. The second fluid 8 can be filled into as well as removed from the second reservoir 7 via openings extending from an outside of the fluid dispenser 1 into the second reservoir 7 (not shown).

As will be explained in greater detail with reference to FIGS. 2 to 6 below the mixing area 18 is in fluid communication with the first receptacle 16 and the second receptacle 17 via a first fluid channel 11 and a second fluid channel 12, respectively. The mixing area 18 is either comprised in a droplet generator 9 that is configured to generate droplets 10 of fluid or the mixing area 18 is in fluid communication with a droplet generator 9' being configured to generate droplets 10 of fluid. In FIGS. 1a to 1d the droplet generator 9, 9' is only schematically indicated by means of a dashed rectangle in order to express that both droplet generator configurations are conceivable. Hence, FIGS. 1a to 1d are mainly intended for illustrating the general working principle of the fluid dispenser 1, wherein particulars about the generation of the cosmetic composition 2 will be discussed in detail with regard to FIGS. 2 to 4.

Figure 1B:
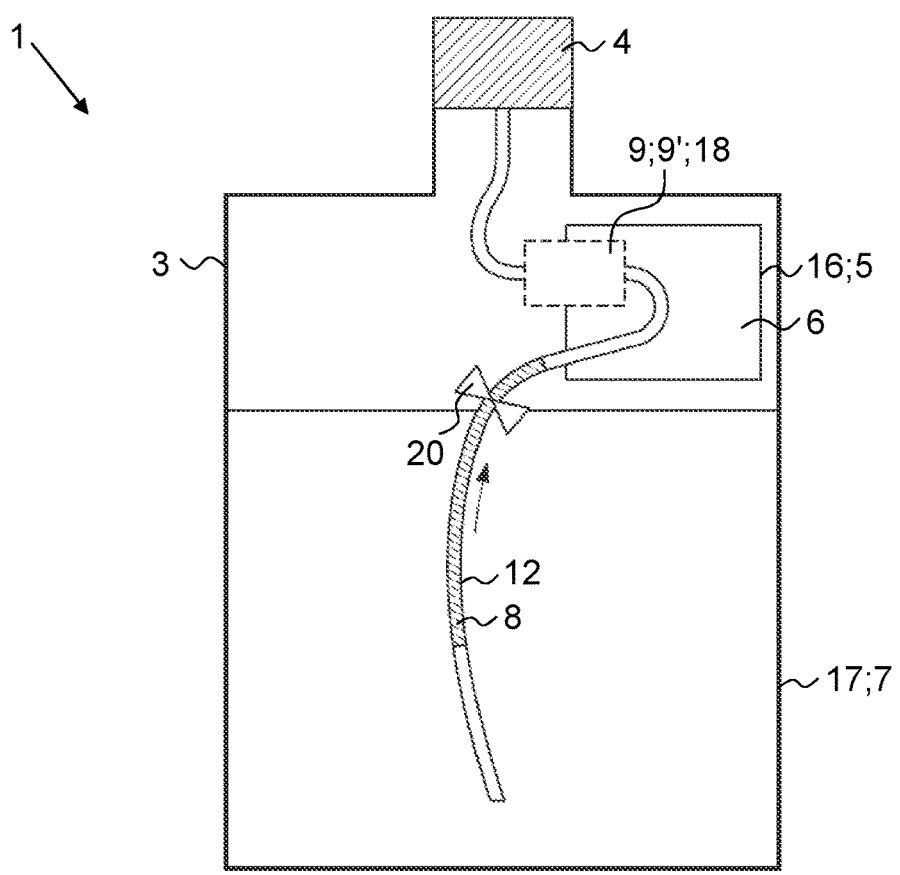
FIG. 1b shows a sectional view of the fluid dispenser according to FIG. 1a in a second position.
Figure 1C:
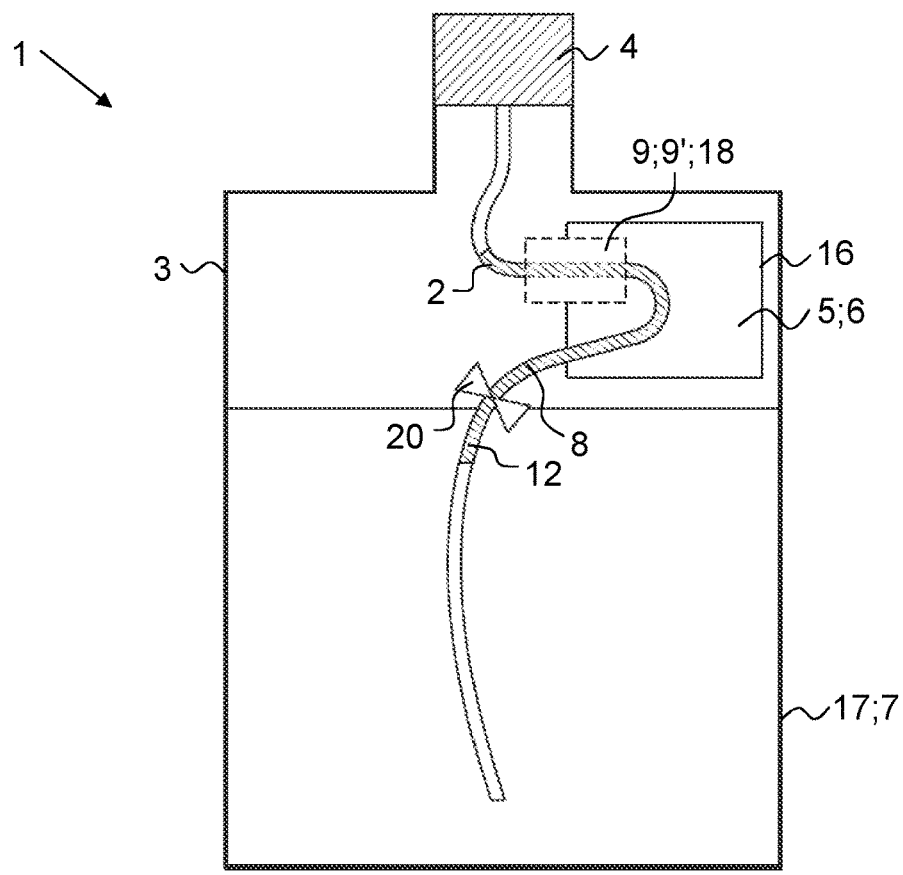
FIG. 1c shows a sectional view of the fluid dispenser according to FIG. 1a in a third position.
Figure 1D:
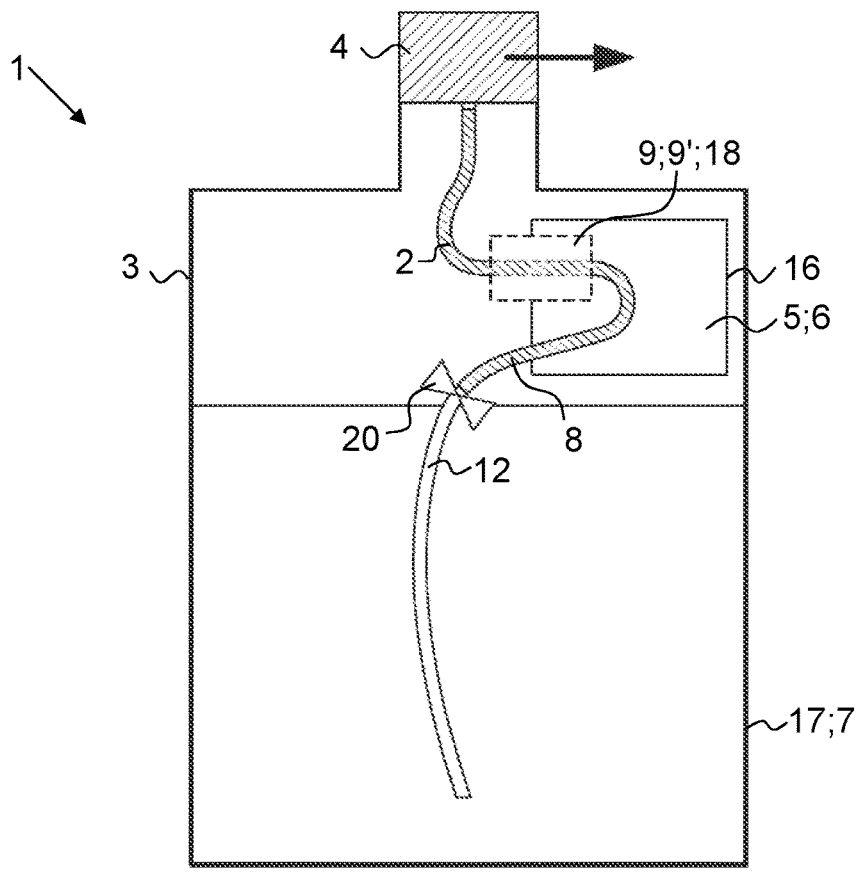
FIG. 1d shows a perspective view of the fluid dispenser according to FIG. 1a in a fourth position.

Namely, and as follows from FIGS. 1a and 1b, upon activation of an activation device (not shown) the activation device transmits an activation signal S to the second receptacle 17 such that a dose of the second fluid 8 is released into the second fluid channel 12. To this end a valve 20 being provided in the second fluid channel 12 and being in communication with the activation device is activated, wherein the activated valve 20 permits a flow of the second fluid 8 along the second fluid channel 12 from the second reservoir 7 past the valve 20. Said second fluid 8 continues to flow into the mixing area 18 being comprised in a droplet generator 9 or being in fluid communication with a droplet generator 9' schematically indicated by the dashed rectangle. Although not shown in the figure also the first receptacle 16 comprises such a valve, the activation of which releases first fluid 6 from the first receptacle 16 into the mixing area 18 via the first fluid channel 11. Hence, in FIG. 1c both the first fluid 6 and the second fluid 8 have flown via the respective fluid channels 11, 12 into the mixing area 18, whereby the cosmetic composition 2 is generated. Said cosmetic composition 2 then flows via the second fluid channel 12 from the mixing area 18 towards the dispenser head 4 and into the dispenser head 4, from which it is then dispensed, see FIG. 1d. As readily follows, the cosmetic composition 2 is generated essentially immediately before it is dispensed.

Figure 2:
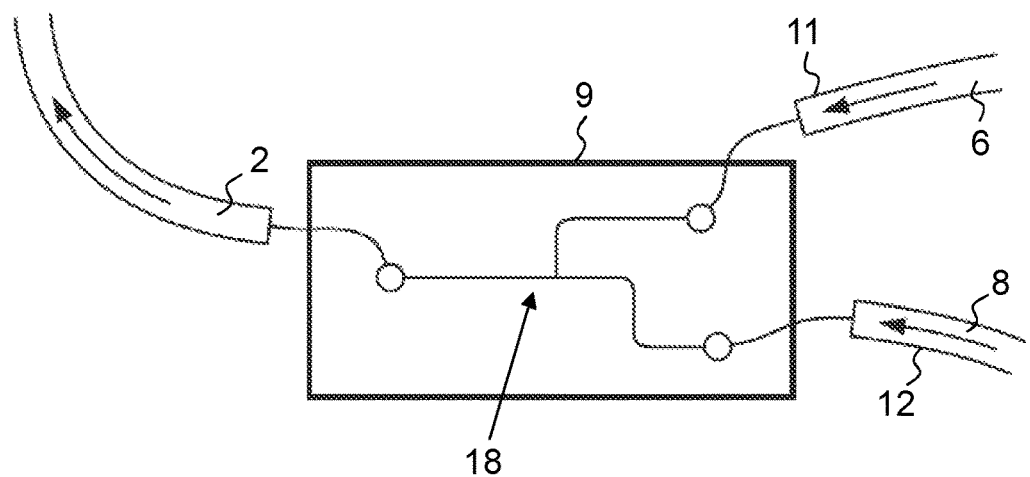
FIG. 2 shows a sectional view of a droplet generator for use in a fluid dispenser according to a first aspect.
Figure 3:
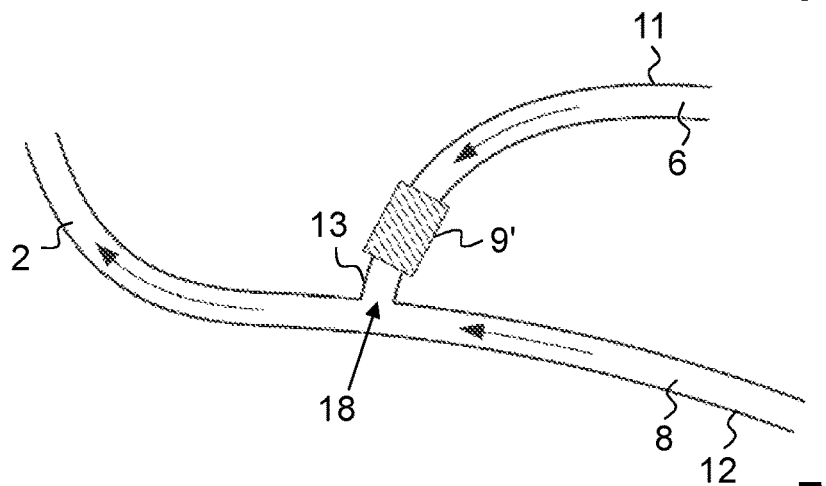
FIG. 3 shows a sectional view of a droplet generator for use in a fluid dispenser according to a further aspect.
Figure 4:
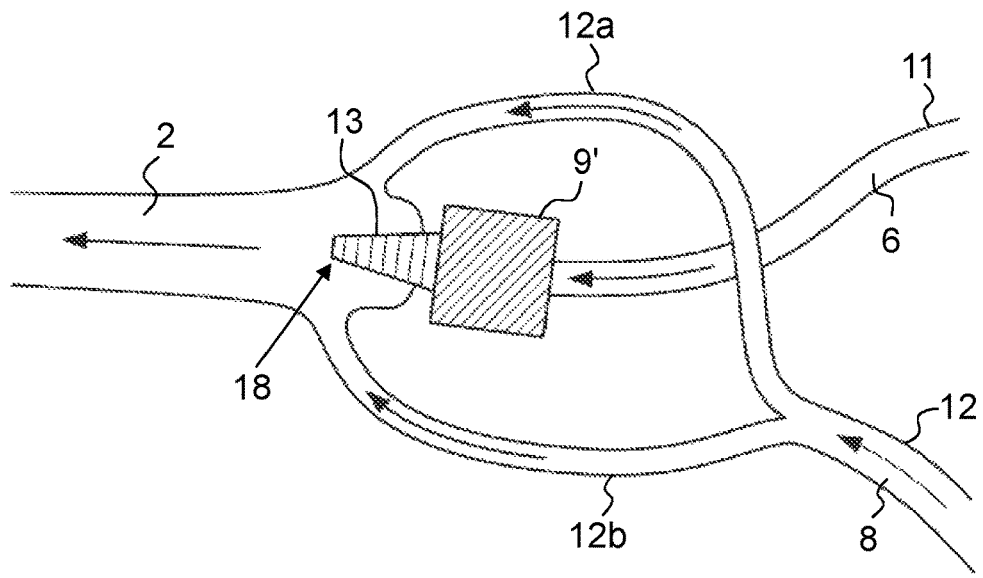
FIG. 4 shows a sectional view of a droplet generator for use in a fluid dispenser according to a further aspect.

As already mentioned, the cosmetic composition 2 can be generated in different ways. For example, the cosmetic composition 2 can be generated by mixing the first and the second fluids 6, 8 with one another. For that purpose the first fluid channel 11 and the second fluid channel 12 can merge into one another, wherein the merging area corresponds to the mixing area 18. This situation is illustrated in FIG. 2, wherein the just described mixing area 18 is comprised in a droplet generator 9. That is, said mixing area 18 is part of a microfluidic device 9. Depending on geometric arrangements such as the diameter of the fluid channels 11, 12 or the angle under which the fluid channels 11, 12 merge into one another and intrinsic parameters of the fluids 6, 8 such as the viscosity the merging of the two fluid channels 11, 12 results in the generation of droplets 10. Here, the first fluid 6 is selected from the group consisting of one or more fragrant essential oils, one or more aroma compounds, or mixtures thereof, and the second fluid 8 corresponds to water, wherein the first fluid channel 11 merges into the second fluid channel 12. As a result, a cosmetic composition 2 comprising droplets 10 of the first fluid 6 being dispersed in the second fluid 8 is generated. The situation illustrated in FIGS. 3 and 4 corresponds to a mixing area 18 being in fluid communication with a droplet generator 9'. In particular, the droplet generator 9' is in fluid communication with the first receptacle 16 by means of the first fluid channel 11, such that the first fluid 6 can flow from the first receptacle 16 into the droplet generator 9'. The droplet generator 9' comprises a droplet generation element such as a piezoelectric element, wherein droplets 10 of the first fluid 6 are generated in the droplet generator 9' upon activation of the droplet generation element. Said droplets 10 of the first fluid 6 are then dispersed in the second fluid 8 flowing in the second fluid channel 12. In FIG. 3 the droplets 10 of the first fluid 6 are dispersed into the second fluid 8 by means of an intermediate fluid channel 13 that connects the droplet generator 9' with the second fluid channel 12. However, it is likewise conceivable to arrange the droplet generator 9' immediately adjacent to the second fluid channel 12 such that the generated droplets 10 of the first fluid 6 are directly dispersed from the droplet generator 9' into the second fluid channel 12, so that the intermediate fluid channel 13 can be omitted. The situation depicted in FIG. 4 differs from the situation according to FIG. 3 in that the second fluid channel 12 is split into two sub-channels 12a, 12b that, with respect to the flow direction of the fluids 6, 8, recombine again after the droplet generator 9'. Hence, the droplet generators 9, 9' differ from one another essentially in the fact that i) droplets of one of the fluids being dispersed in the other of the fluids are generated during a particular interaction of the two fluids in case of the droplet generator 9 depicted in FIG. 2 and that ii) droplets of only one of the fluids are generated at first and that said droplets are subsequently dispersed in the other fluid in case of the droplet generators 9' depicted in FIGS. 3 and 4.

Figure 5:
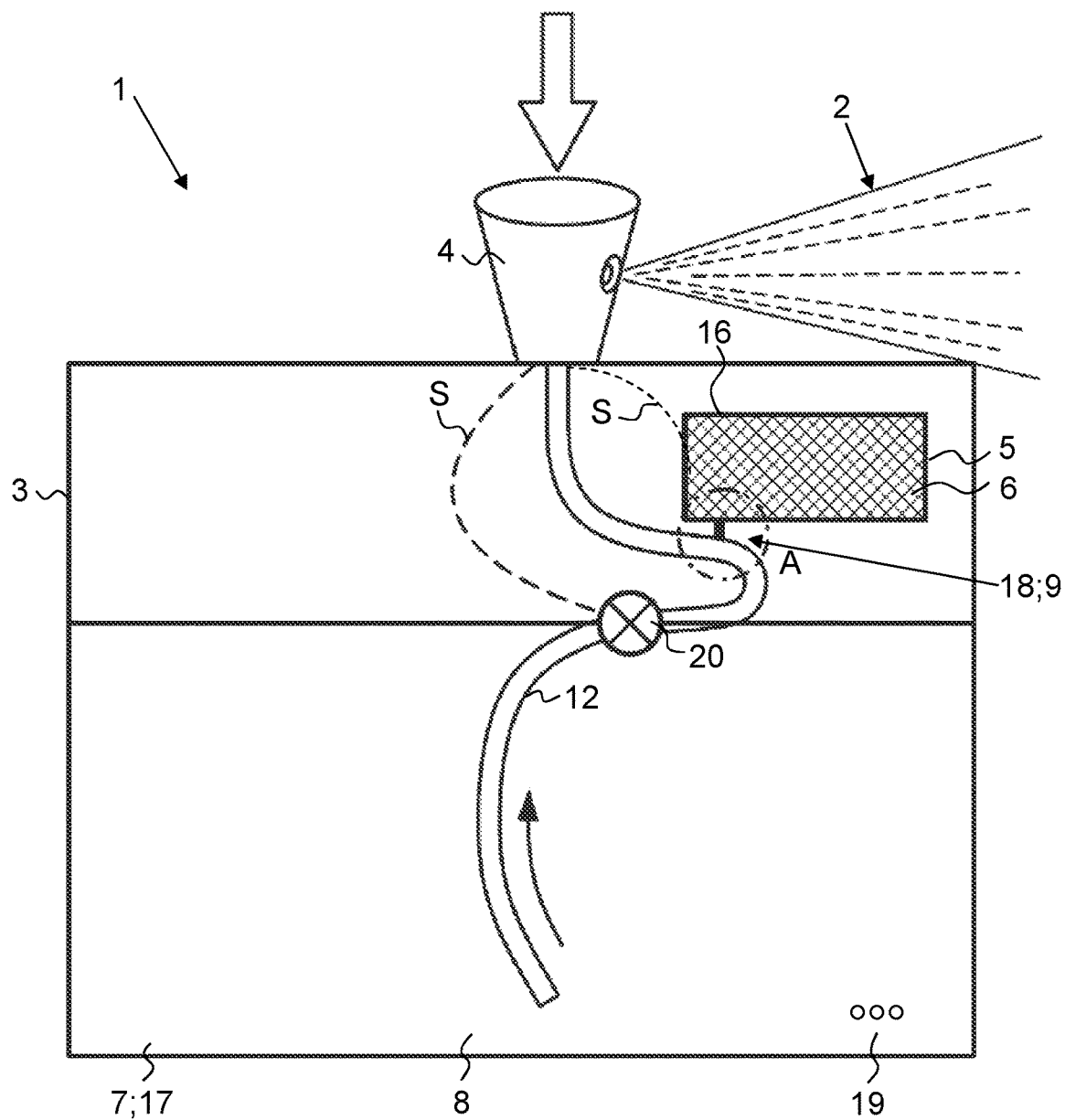
FIG. 5 shows a sectional view of a fluid dispenser comprising a droplet generator according to the first aspect.
Figure 6:
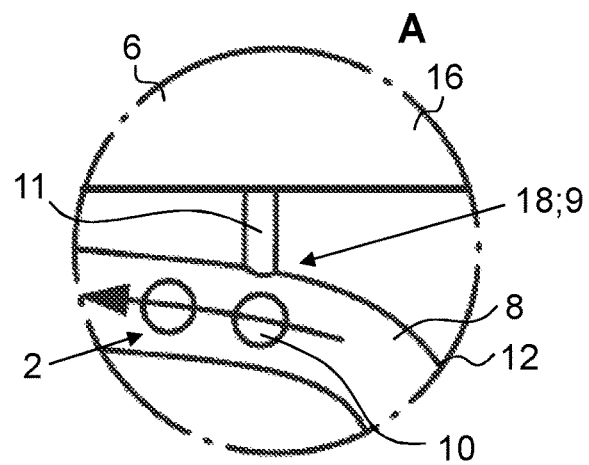
FIG. 6 shows an enlarged view of section A of FIG. 5.
Figure 9A:
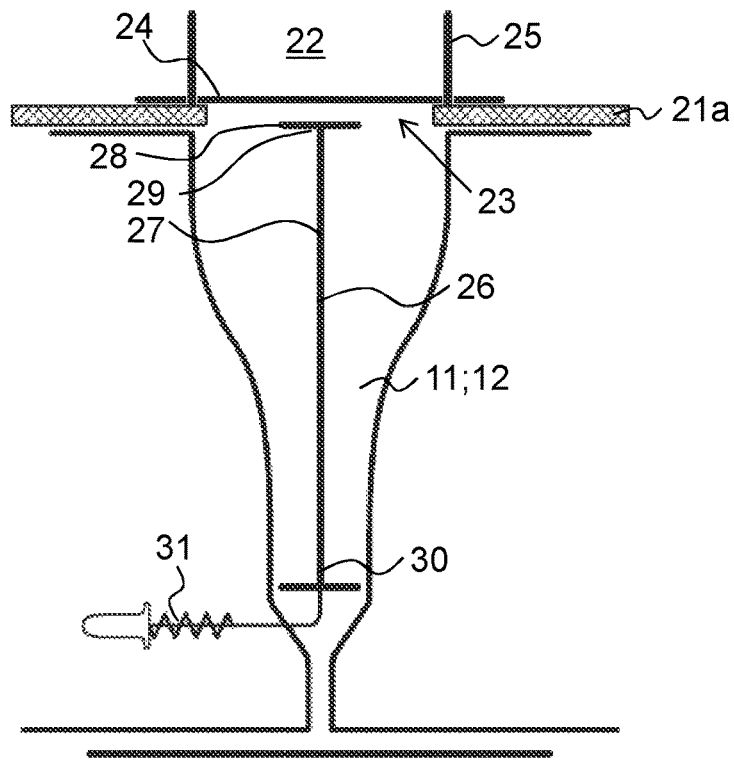
FIG. 9a shows a partial sectional view through the fluid dispenser comprising a capsule and an actuation element according to a further aspect in the closed position.
Figure 9B:
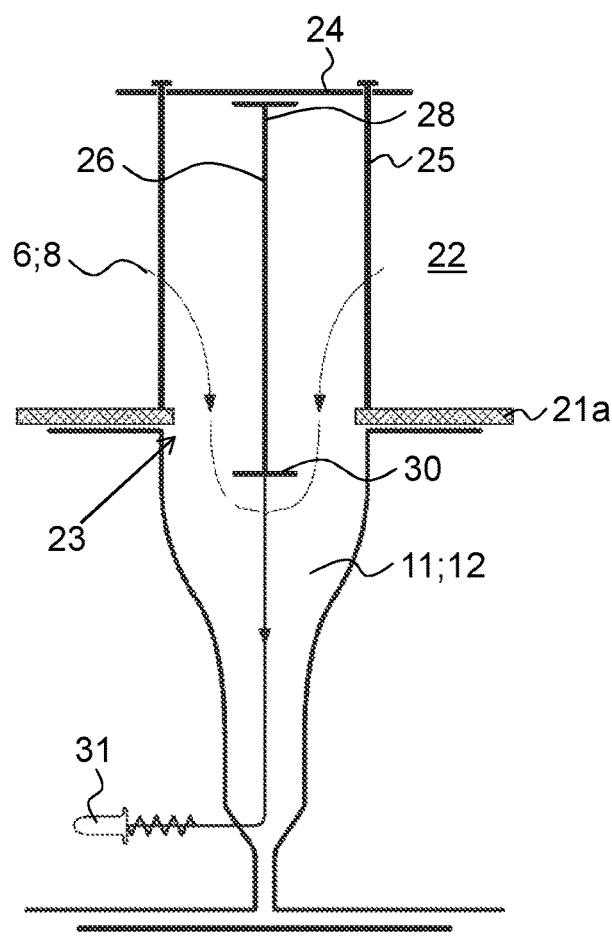
FIG. 9b shows a partial sectional view of the fluid dispenser comprising the capsule and the actuation element according to the further aspect in the opened position.

In FIG. 5 a fluid dispenser 1 is depicted which again comprises a first receptacle 16 in which a first reservoir 5 in the form of a capsule comprising the first fluid 6 is arranged and a second receptacle 17 having an integrally formed second reservoir 7 into which the second fluid 8 is filled. Moreover, the first and second receptacle 16, 17 is in each case in fluid communication with a mixing area 18 by means of first and second fluid channels 11, 12. As best seen in FIG. 6, the fluid dispenser 1 according to this example comprises a mixing area 18 being formed by the merging area of the first and second fluid channels 11, 12. That is, the present fluid dispenser 1 comprises a droplet generator 9 being configured as a microfluidic device, wherein droplets 10 of the first fluid 6 are generated within the second fluid 8 upon the dispersion of the first fluid 6 in the second fluid 8. Here, the dispenser head 4 is designed as an atomizer, wherein the cosmetic composition 2, once it has been generated in the mixing area 18, can be sprayed from the dispenser 1 and be applied onto a user. Moreover, the fluid dispenser 1 can further comprise a level indicator 19 being configured to indicate the amount of first fluid 6 in the first reservoir 5 and/or the amount of second fluid 8 in the second reservoir 7 in order to timely inform a user about expiring fluid contents of said reservoirs 5, 7. The level indicator 19 can be provided by means of an indicator light arranged on the housing 3 which is in communication with sensing means provided in the first and second reservoir 5, 7 and being configured to sense the amount of fluid 6, 8 comprised in said reservoirs 5, 7. Said sensing means could be a weight sensor measuring the weight of the fluid 6, 8 in the reservoirs 5, 7.

FIGS. 7a to 9b illustrate details about the first and/or second reservoir 5, 7 in the form of a capsule comprising the first fluid 6 and the second fluid 8, respectively. That is, the fluids 6, 8 can be provided in the fluid dispenser 1 by means of a reservoir 5, 7 having the shape of a capsule. In the present figures said capsule 5, 7 takes a rectangular outline. However, any other forms are conceivable, too. For example, the capsule 5, 7 could have a circular, oval or polyhedral form. In the case of the rectangular capsule 5, 7, said capsule 5, 7 is constituted by six capsule walls 21a-21f which define an interior space 22 into which the fluid 6, 8 can be filled. In order to allow a filling and removal of fluid 6, 8 from the capsule 5, 7, the capsule 5, 7 comprises an aperture 23. In a closed state of the capsule 5, 7, i.e. in a state where no fluid 6, 8 shall be dispensed from the capsule 5, 7, the aperture 23 is closed by means of a closing element 24. Here, the closing element 24 is provided by means of a membrane. To this end the diameter dc of the membrane is larger than the diameter da of the aperture 23 in the capsule wall 21a. In order to allow an opening of the capsule aperture 23 in an opened state, i.e. in a state where fluid 6, 8 shall be dispensed from the capsule 5, 7, the membrane 24 is slidingly arranged on guide rails 25. Said guide rails 25 are mounted in the interior space 22 of the capsule 5, 7 and extend from the capsule wall 21a comprising the aperture 23 towards the opposite capsule wall 21f. As best seen in FIGS. 8a and 8b, the fluid dispenser 1 comprises an actuation element 26 which is configured to interact with the membrane 24 so as to open and close the aperture 23. In particular, in order to open the aperture 23, the actuation element 26 presses against the membrane 24 of the capsule 5, 7, whereby the membrane 24 slides along the guide rails 25 from the capsule aperture 23 towards the interior space 22 of the capsule 5, 7. As a result the aperture 23 of the capsule 5, 7 is released and the fluid 6, 8 comprised within the capsule 5, 7 is allowed to leave the capsule 5, 7. In the present example the actuation element 26 is arranged within the fluid channel 11, 12 that connects the receptacle 16, 17 with the mixing area 18, see FIGS. 9a and 9b. Moreover, the capsule 5, 7 can be arranged in the fluid dispenser 1 such that its aperture 23 is facing the fluid channel 11, 12. By actuating the actuation element 26 the membrane 24 is displaced towards the interior space 22 of the capsule 5, 7, whereby the aperture 23 is released and the fluid 6, 8 can flow from within the capsule 5, 7 into the fluid channel 11, 12 based on the gravitational force and/or other forces. In these figures the actuation element 26 is comprised of a plunger 27 with a piston 28 on its distal end 29. On its proximal end 30 the actuation element 26 is connected to a biased spring element 31. Said biased spring element 31 is in turn in connection with the activation device, wherein, upon activation of the activation device, the spring force exerted by the spring element 31 is overcome, the actuation element 26 is displaced and the aperture 23 in the capsule 5, 7 is released because of the pressing force exerted on the membrane 24 by the piston 28. Upon a deactivation of the activation device the actuation element is transferred due to the biasing spring force exerted by the spring element 31 into its initial position. In said initial position the aperture 23 of the capsule 5, 7 is again closed by the membrane 24. In order to facilitate a closing of the aperture 23 it is conceivable that the membrane 24 and the piston 28 of the actuation element 26 comprise mutually attracting magnetic elements, wherein the magnetic force between the magnetic elements pulls the membrane 24 into the closed position when the actuation element 26 is transferred in its initial position. When the aperture 23 of the capsule 5, 7 is closed by the closing element 24, the capsule can be removed from the fluid dispenser without that its content is getting lost. As a consequence, a capsule not being empty can be removed from the fluid dispenser and can be re-used again at a later stage. This aspect is of relevance for example in case that a user wishes to temporarily use a capsule comprising another fluid.

Figure 10:
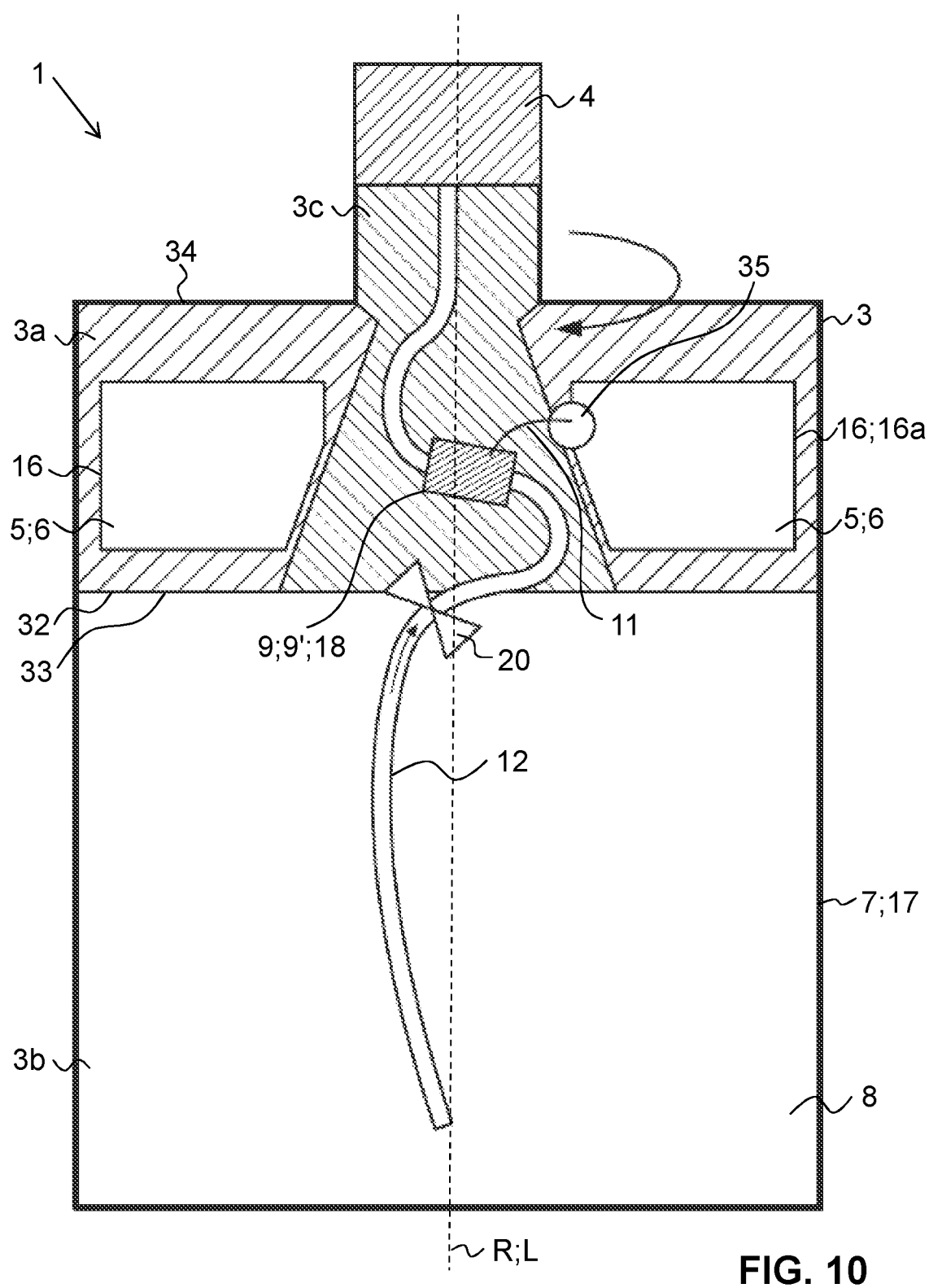
FIG. 10 shows a sectional view of a fluid dispenser according to a further aspect.

In order to allow a convenient generation of different cosmetic compositions 2 the fluid dispenser 1 can comprise two or more first receptacles 16 and/or two or more second receptacles 17 that are in each case connectable to a first reservoir 5 and a second reservoir 7 comprising different first and second fluids 6, 8, respectively. For example, the different first fluids 6 could differ in the particular fragrant essential oils or aroma compounds they are made of and the different second fluids 8 could correspond to different aqueous solutions. To this end a fluid dispenser 1 comprising a multi-part housing 3 is provided. Such a fluid dispenser 1 is depicted in FIG. 10, wherein the multi-part housing 3 is constituted by a first housing part 3a, a second housing part 3b and a third housing part 3c, wherein the first housing 3a part is designed so as to be rotatable with respect to the second and third housing parts 3b. 3c. In particular, the first housing part 3a is rotatable about a rotational axis R extending along a central longitudinal axis L of the fluid dispenser 1. The first housing part 3a comprises three first receptacles 16, wherein a first reservoir 5 in the form of a capsule comprising a first fluid 6 is inserted into each first receptacle 16. The second housing part 3b comprises a second receptacle 17 being integrally formed with the second housing part 3b. The third housing part 3c extends from a lower end 32 of the first housing part 3b being adjacent to an upper end 33 of the second housing 3b part centrally through the first housing part 3a and beyond an upper end 34 of the first housing part 3a. The dispenser head 4 is provided on the third housing part 3c and the mixing area 18 is arranged within the third housing part 3c. The mixing area 18 is in fluid communication with one of the first receptacles 16 via a first fluid channel 11 and with the second receptacle 17 via a second fluid channel 12. To this end it is irrelevant whether the mixing area 18 is comprised in a droplet generator 9 as discussed above with reference to FIG. 2 or in fluid communication with a droplet generator 9' as discussed above with reference to FIGS. 3 and 4. Both droplet generator configurations are conceivable. The second fluid channel 12 is arranged within the second housing part 3b and the third housing part 3c and extends from the second reservoir 7 via the mixing area 18 towards the dispenser head 4. As a result, the second fluid channel 12 and the mixing area 18 are not rotated during a rotation of the first housing part 3a but remain stationary. At the boundary to the first housing part 3a an interface 35 is provided in the third housing part 3c. Said interface 35 serves the purpose of a docking point for one of the first receptacles 16 the fluid 6 of which shall be used for the generation of the cosmetic composition 2. This first receptacle 16 is hereinafter referred to as the active first receptacle 16a. To this end the interface 35 is configured to establish a fluid communication between the mixing area 18 and the active first receptacle 16a via the first fluid channel 11.

Figure 11A:
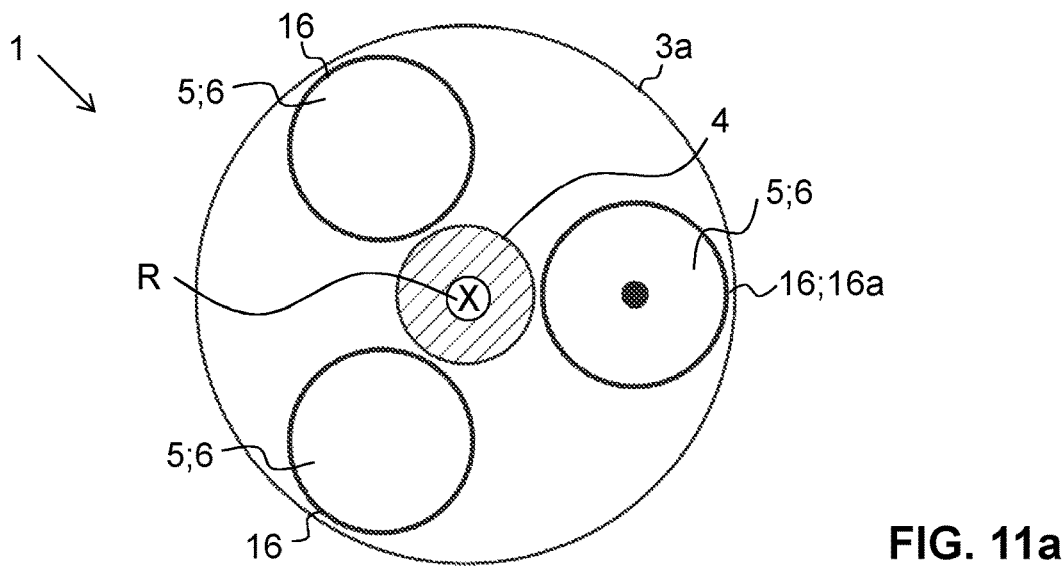
FIG. 11a shows a top sectional view of a fluid dispenser according to a further aspect in a first position.
Figure 11B:
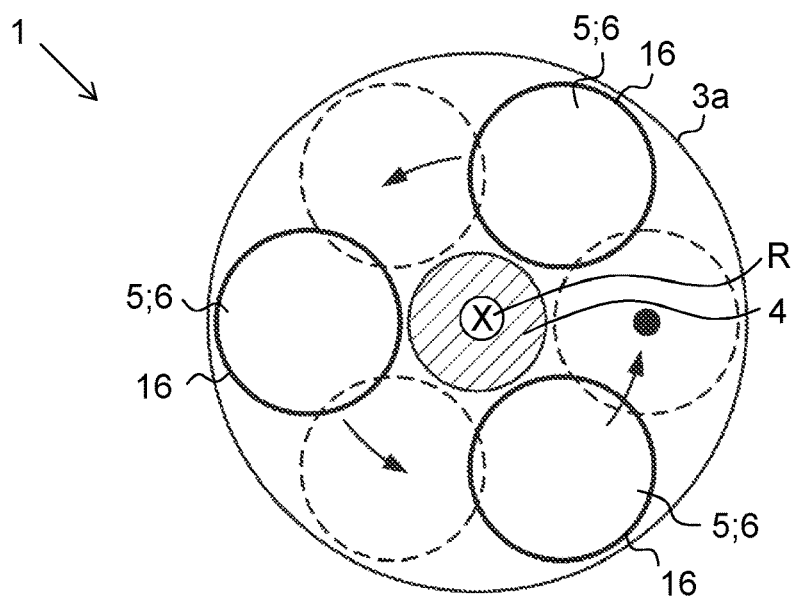
FIG. 11b shows a top sectional view of the fluid dispenser according to FIG. 11a in an intermediate position.
Figure 11C:
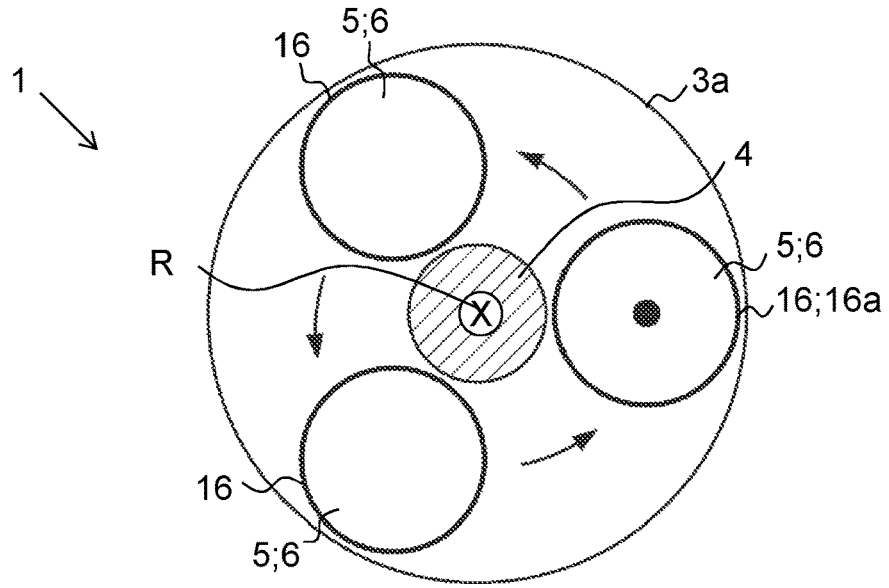
FIG. 11c shows a top sectional view of the fluid dispenser according to FIG. 11a in a second position.

With respect to FIGS. 11a to 11c the generation of different cosmetic compositions 2 by means of a fluid dispenser 1 according to FIG. 10 is schematically illustrated. In these figures the fluid dispenser 1 is depicted as a sectional view seen from the top so as to illustrate the centrally arranged and here circular dispenser head 4 and the three first receptacles 16 with three in this case circular capsules 5 comprising different first fluids 6 disposed around the dispenser head 4. In a first position depicted in FIG. 11a the mixing area 18 is in fluid communication with the second receptacle 17 and the second fluid 8 comprised therein and with the active first receptacle 16a and the first fluid 6 comprised therein. If a user wishes to change the chemical composition of the cosmetic composition 2 he rotates the first housing part 3a about the rotational axis R. The fluid dispenser 1 is thereby brought into an intermediate position depicted in FIG. 11b, wherein none of the first receptacles 16 is in fluid communication with the mixing area 18. The dashed circles in FIG. 11b indicate the positions required for the first receptacles 16 in which a fluid communication between the active receptacle 16a and the mixing area could be established. If a user now activates the activation device, only the residual cosmetic composition 2 comprised in the fluid dispenser 1 is dispensed from the fluid dispenser 1. However, no new cosmetic composition 2 is generated. This step can thus be seen as a cleaning step. If the user rotates the first housing part 3a further about the rotational axis R another first receptacle 16 becomes the active first receptacle 16a, see FIG. 11c. In this second position the mixing area 18 is again in fluid communication with the second receptacle 17 and the second fluid 8 comprised therein as well as with this other active first receptacle 16a and the first fluid 6 comprised therein. If the activation device is activated, a cosmetic composition 2 being different from the cosmetic composition 2 generated in the first position according to FIG. 11a is generated.

With reference to FIGS. 12 to 18 different aspects of a dispensing arrangement 38, a first dosing arrangement 36 and a second dosing arrangement 37 of a fluid dispenser 1 are discussed. In any case, said dispensing arrangement 38 is configured to actuate the first dosing arrangement 36 and the second dosing arrangement 37 upon its actuation. For the sake of clarity certain aspects of the fluid dispenser 1 such as the housing 3 or the first and second reservoirs 5, 7 have been omitted in a majority of these figures. However, it should be noted that the first dosing arrangement 36 can be provided in the housing 3 or on the first reservoir 5 or in the first reservoir 5 or in the dispenser head 4. Likewise, the second dosing arrangement 37 can be provided in the housing 3 or on the second reservoir 7 or in the second reservoir 7 or in the dispenser head 4. The first dosing arrangement 36 is in fluid communication with the first receptacle 16 and the mixing area 18 and is configured to generate upon actuation by the dispensing arrangement 38 the dose of the first fluid 6. Also the second dosing arrangement 37 is in fluid communication with the second receptacle 17 and the mixing area 18 and is configured to generate upon actuation by the dispensing arrangement 38 a dose of the second fluid 8. Hence, upon actuation of the first dosing arrangement 36 and of the second dosing arrangement 37, doses of the first fluid 6 and the second fluid 8 will be generated by the dosing arrangements 36, 37 and will flow into the mixing area 18, whereby the cosmetic composition 2 is generated. In the depicted embodiments the mixing area 18 is provided within a mixing chamber 39, and wherein the first receptacle 16, the second receptacle 17 and the dispenser head 4 are in fluid communication with the mixing chamber 39. The mixing chamber 39 can arranged within the housing 3 or within the dispenser head 4. The dispensing arrangement 38 is configured to actuate the first dosing arrangement 36 and the second dosing arrangement 37 simultaneously or temporally delayed with respect to one another. The dispensing arrangement 38 is further configured to transfer the cosmetic composition 2 from the mixing area 18 to the dispenser head 4 for dispensing. An actuation of the first dosing arrangement 36 and the second dosing arrangement 37 by the dispensing arrangement 38 preferably occurs in a first step and a transfer of the cosmetic composition 2 from the mixing area 18 to the dispenser head 4 occurs in a second step taking place after the first step as seen in time.

In the embodiments shown in FIGS. 12 to 16 the dispensing arrangement 38 is configured such that the first dosing arrangement 36 is actuated by means of a first dosing arrangement trigger signal that is generated by the dispensing arrangement 38 upon its actuation by a user. However, an actuation of the second dosing arrangement 37 is effectuated mechanically in FIGS. 12 and 13 and by means of a second dosing arrangement trigger signal being produced by the dispensing arrangement 38 in FIGS. 14a to 16. In the embodiment according to FIG. 18 both the first dosing arrangement 36 and the second dosing arrangement 37 are actuated mechanically.

In the embodiments depicted in FIGS. 12 to 16 the first dosing arrangement 36 in each case corresponds to a micropump that is arranged in a fluid channel 51 connecting the first receptacle 16 with the mixing area 18. That is, the dispensing arrangement 38 and the first dosing arrangement 36 are configured separately from one another and are in fluid connection with one another via the fluid channel 51. The micropump 36 is configured such, that it generates the dose of the first fluid 6 upon receipt of a first dosing arrangement trigger signal that is produced by the dispensing arrangement 38 upon actuation of the dispensing arrangement 38 by the user. The second dosing arrangement 37 however is provided by means of a piston pump, see FIGS. 12 and 13, or by means of a micropump, see FIGS. 14a, 15 and 16. As will be explained below, an actuation of the second dosing arrangement 37 in the form of the piston pump occurs mechanically, whereas an actuation of the second dosing arrangement 37 in the form of a micropump occurs by means of a second dosing arrangement signal that is again produced by the dispensing arrangement 38 upon actuation of the dispensing arrangement 38 by the user.

Figure 12:
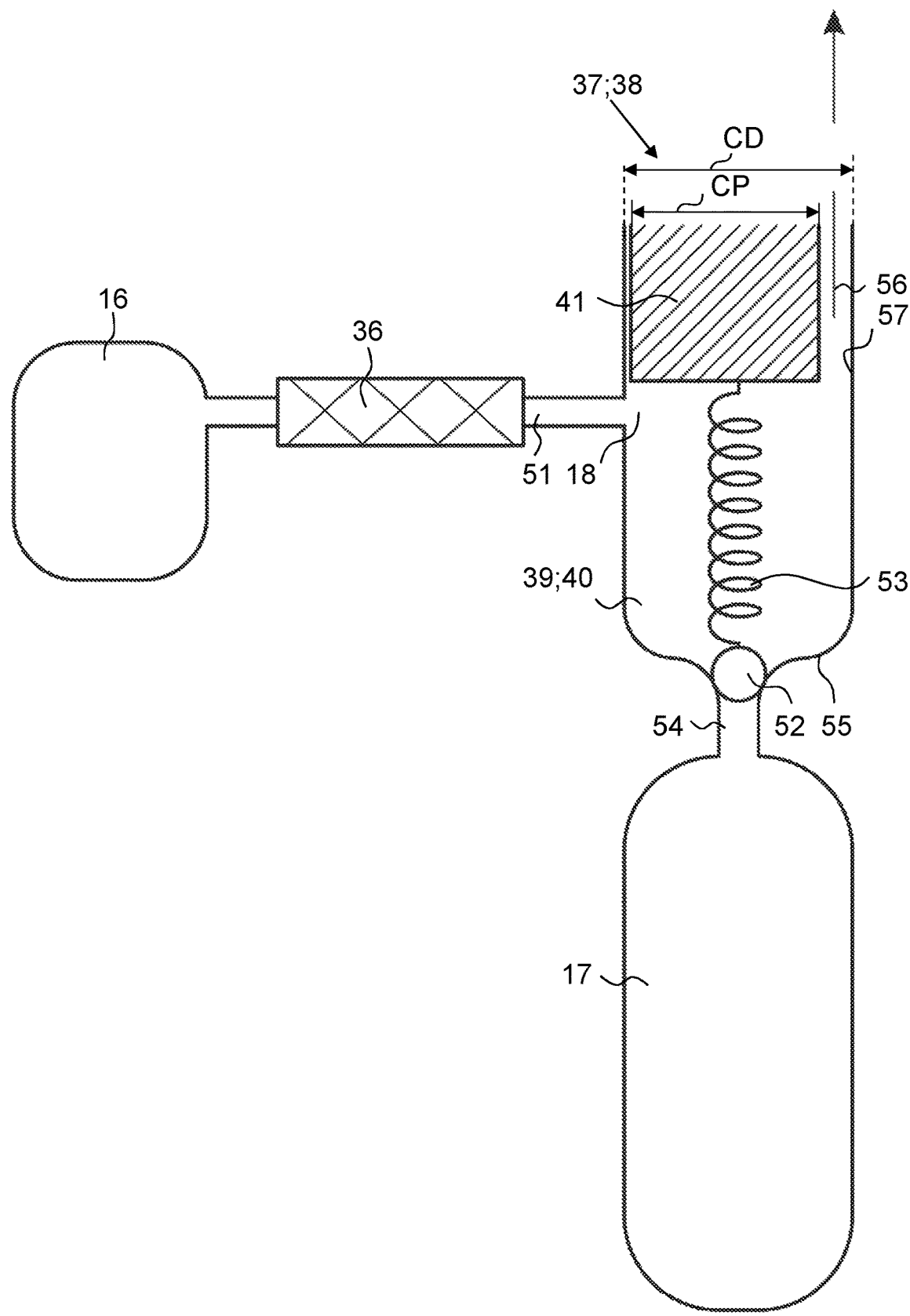
FIG. 12 shows a sectional view of a dispensing arrangement, a first dosing arrangement and a second dosing arrangement of a fluid dispenser according to a further aspect.
Figure 13:
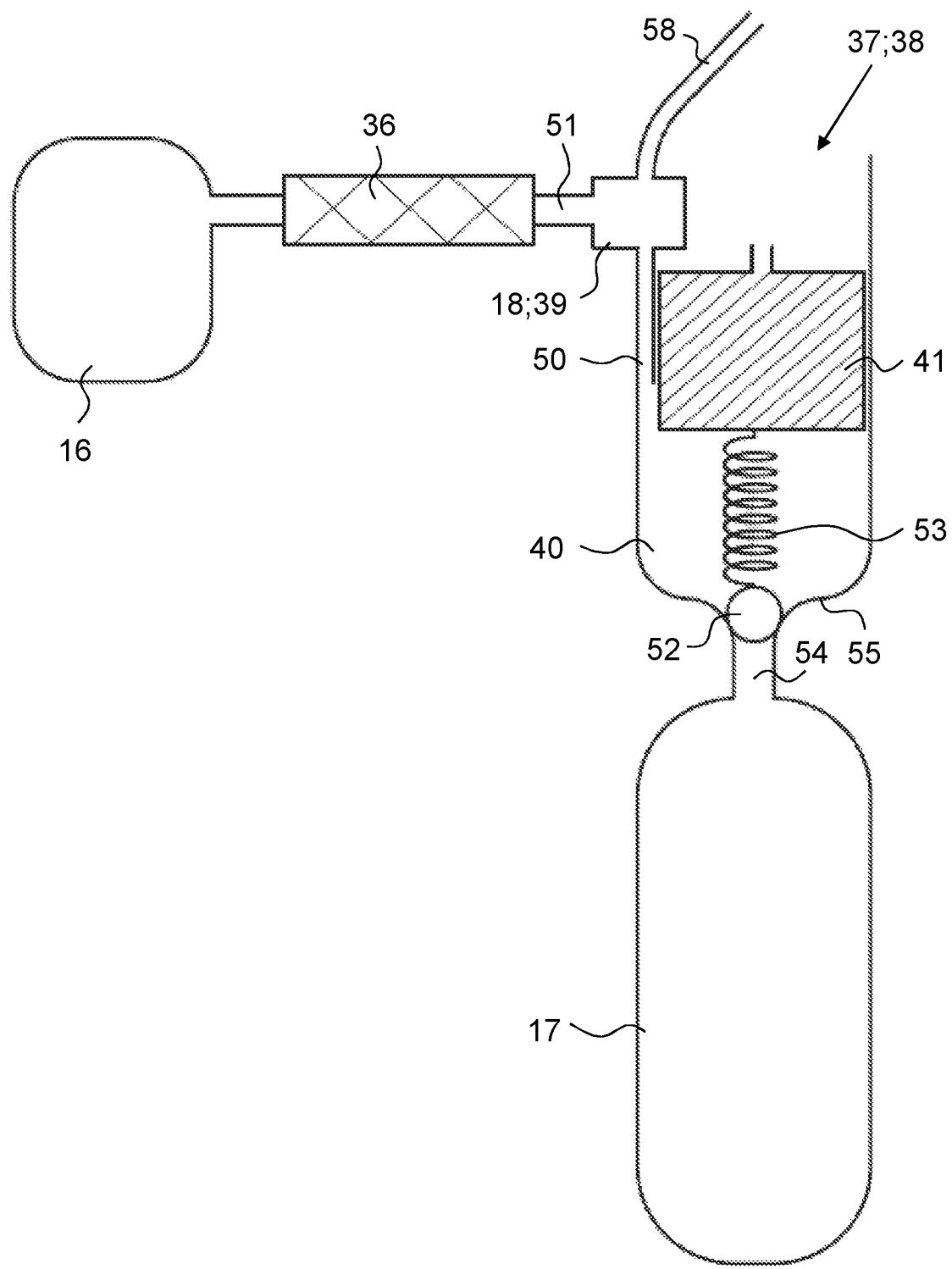
FIG. 13 shows a sectional view of a dispensing arrangement, a first dosing arrangement and a second dosing arrangement of a fluid dispenser according to a further aspect.

If the second dosing arrangement 37 is provided by means of a piston pump, it is preferred that the dispensing arrangement 38 comprises a dispensing chamber 40 and an actuating element 41 that is arranged within the dispensing chamber 40, see FIGS. 12 and 13. The dispensing chamber 40 is in fluid communication with the mixing chamber 39 and the dispenser head 4. The actuating element 41 corresponds to a spring-loaded piston that is displaceably mounted within the dispensing chamber 40. The dispensing arrangement 38 is configured such, that the cosmetic composition 2 is transferable from the mixing chamber 39 to the dispenser head 4 upon an actuation of the piston 41. As readily follows from these figures, the piston pump 37 comprises a piston 41 that is displaceably arranged within the dispensing chamber 40. Moreover, the piston 41 of the second dosing arrangement 37 in the form of the piston pump 37 corresponds to the actuating element 41 in the form of the piston 41 of the dispensing arrangement 38. Consequently, the dispensing arrangement 38 comprises at least part of the second dosing arrangement 37 in the form of the piston pump 37. A ball 52 is disposed in a valve seat that is provided in a tubing or channel 54 connecting the second receptacle 17 with the dispensing chamber 40. Furthermore, and although not depicted in the figures, the piston 41 is in connection with the dispenser head 4. If the user actuates the dispenser head 4, for example by pressing it downwards towards the housing 3, the piston 41 is thereby actuated as well. In particular, the piston 41 is moved downwards, wherein any fluid being present in the dispensing chamber 40 is displaced during this movement. The embodiments depicted in FIGS. 12 and 13 differ from one another in that the dispensing chamber 40 corresponds to the mixing chamber 39 in the embodiment of FIG. 12, whereas the dispensing chamber 40 and the mixing chamber 39 are configured separately from one another and are in fluid connection with one another via a fluid channel 50 in the embodiment of FIG. 13. Furthermore, in the former case depicted in FIG. 12 the fluid channel 51 leads from the first dosing arrangement in the form of the micropump 36 into the dispensing chamber 40, which dispensing chamber 40 therefore corresponds here to the mixing chamber 39. The cosmetic composition 2 is thus generated in the dispensing chamber 40 corresponding to the mixing chamber 39. If the actuating element 41 in the form of the piston is actuated, the cosmetic composition 2 is transferred from the dispensing chamber 40 being the mixing chamber 39 to the dispenser head 4 for dispensing. In the latter case depicted in FIG. 13 the fluid channel 51 leads from the first dosing arrangement in the form of the micropump 36 into the mixing chamber 39, which is in fluid connection with the dispensing chamber 40 via the fluid channel 50. If the actuating element 41 in the form of the piston is actuated, second fluid 8 is transferred from the dispensing chamber 40 into the mixing chamber 39, whereby the cosmetic composition 2 is generated, and which cosmetic composition 2 is subsequently transferred from the mixing chamber 39 to the dispenser head 4 for dispensing. In both cases the dispensing arrangement 38, i.e. the second dosing arrangement 37, is configured such, that the second fluid 8 is automatically transferable from the second reservoir 7 into the dispensing chamber 40 after the actuation of the piston 41. An actuation of the piston 41 corresponds to a displacement of the piston 41 against the spring-force exerted by the spring 53. For example, by pushing the dispenser head 4 downwards, the piston 41 is moved downwards towards a bottom wall 55 of the dispensing chamber 40 into a compressed state, wherein the spring 53 is compressed. If the user then releases the dispenser head 4, the compressed spring 53 will automatically, i.e. without any external impact, move the piston 41 from its compressed state into an uncompressed state. During this movement second fluid 8 is pulled from the second reservoir 7 into the dispensing chamber 40 as a result of capillary forces and/or a pressure difference caused by the moving piston 41. Consequently, in a rest state, i.e. after an actuation but before any further actuation of the dispensing arrangement 38, second fluid 8 will be present in the dispensing chamber 40. A transfer of the cosmetic composition 2 from the mixing area 18 to the dispenser head 4 in FIGS. 12 and 13 occurs in different ways. Namely, in the embodiment of FIG. 12 a cross-section CD of the dispensing chamber 40 is larger than a cross-section CP of the piston 41, such that a fluid channel 56 is formed between the piston 41 and an inner wall 57 of the dispensing chamber 40. Upon actuation of the piston 41, the cosmetic composition 2 can flow from the dispensing chamber 40, i.e. here the mixing chamber 39, through said fluid channel 56 into the dispenser head 4 for being dispensing from the fluid dispenser 1. Other configurations are however likewise conceivable. For example, a fluid channel could extend through the piston and/or through the spring that is spring-loading the piston. In the embodiment depicted in FIG. 13, however, a separate fluid channel 58 is extending from the mixing chamber 39, which separate fluid channel 58 connects the mixing chamber 39 with the dispenser head 4 such, that the cosmetic composition 2 can be dispensed from the mixing chamber 39 through the dispenser head 4 via said separate fluid channel 58.

Figure 14A:
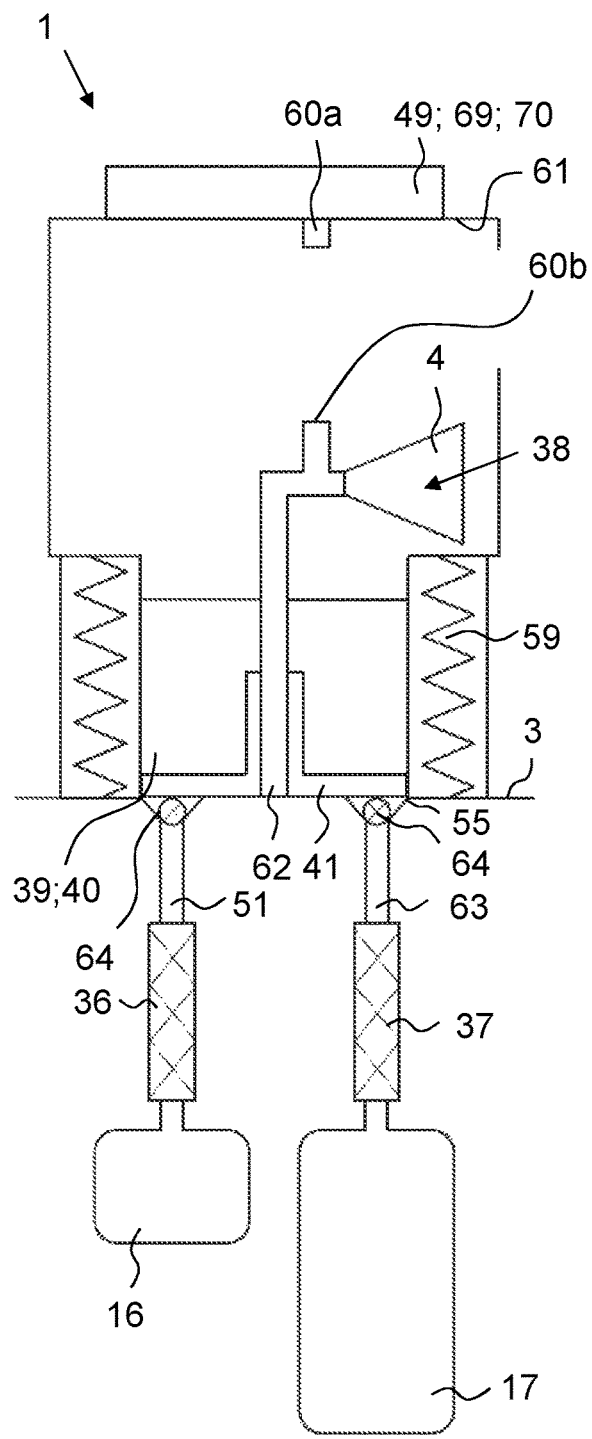
FIG. 14a shows a sectional view of a dispensing arrangement, a first dosing arrangement and a second dosing arrangement of a fluid dispenser according to a further aspect in a first position.
Figure 14B:
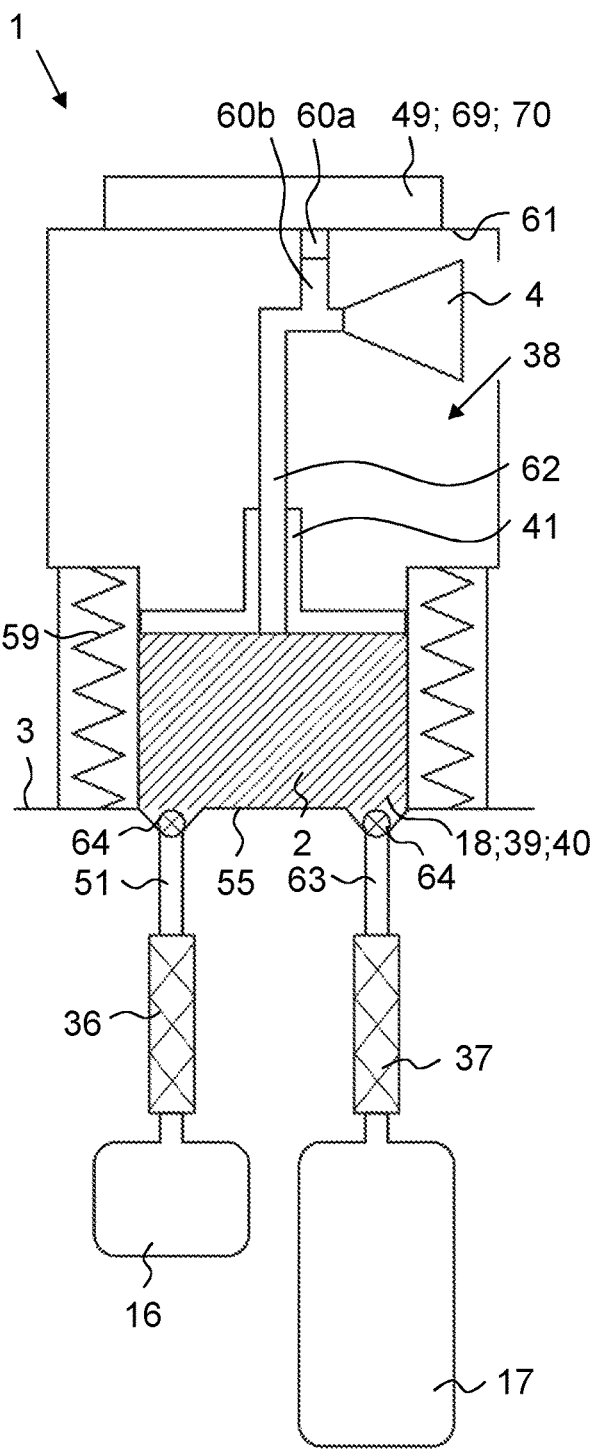
FIG. 14b shows a sectional view of the dispensing arrangement of the fluid dispenser according to FIG. 14a in a second position.

In the fluid dispenser 1 depicted in FIGS. 14a and 14b the dispensing arrangement 38 likewise comprises an actuating element 41 in the form of a piston that is displaceably mounted within the dispensing chamber 40, wherein the dispensing chamber 40 corresponds to the mixing chamber 39. However, this fluid dispenser 1 differs from the fluid dispensers 1 according to FIGS. 12 and 13 in that the second dosing arrangement 37, like the first dosing arrangement 36, corresponds to a micropump and in that the dispenser head 4 is spring-loaded and displaceably arranged on the housing 3. That is, the dispensing arrangement 38 does not comprise the second dosing arrangement 37. Furthermore, the dispensing arrangement 38 is configured such, that the piston 41 is movable from an initial position to a final position during a flow of first fluid 6 and/or of second fluid 8 into the dispensing chamber 40, i.e. the mixing chamber 39. In the initial position, wherein no fluid is present in the dispensing chamber 40, the piston rests on a bottom wall 55 of the dispensing chamber 40. This situation is depicted in FIG. 14a. If fluid 6, 8 is dispensed by the dosing arrangements 36, 37 into the dispensing chamber 40, the fluids 6, 8 increasingly move the piston 41 away from the bottom wall 55 of the dispensing chamber 40 and into a final position, wherein the piston 41 is spaced apart from said bottom wall 55. This situation is depicted in FIG. 14b. In the initial position, the dispenser head 4 is spaced apart from the housing 3 by a first distance as a result of its spring-loaded design. In the second position, the dispenser head 4 has been moved against the spring-force exerted by the spring 59 that connects the dispenser head 4 with the housing 3 and towards the housing 3 such that it is spaced apart from the housing 3 by a second distance being smaller than the first distance. Also in this case the dispenser head 4 and the piston 41 are operatively connected with one another such, that the movement of the dispenser head 4 from its final position into its initial position results in a movement of the piston 41 from its final position into its initial position, whereby the cosmetic composition 2 being present in the mixing chamber 39 is transferred to the dispenser head 4. The operative connection between the dispenser head 4 and the piston 41 is achieved by means of a releasable connection that is established between a first connection element 60a disposed on an upper wall 61 of the dispenser head 4 and a second connection element 60b disposed on the piston 41. These first and second connection elements 60a, 60b can correspond to magnetic elements that establish a magnetic attraction between one another or they are configured to enter a plug connection or push-in connection, for example. If the piston 41 is moved upwards because of fluid 6, 8 flowing into the dispensing chamber 40, its second connection element 60b is brought into contact with the first connection element 60a of the dispenser head 4. If the user then actuates the dispenser head 4 by pressing it downwards, the connection between the connection elements 60a, 60b results in a downward movement of the piston 41 as well. In contrast to the embodiments according to FIGS. 12 and 13, the cosmetic composition 2 is thereby dispensed from the dispenser head 4 through a fluid channel 62 that extends through the piston 41. The micropumps 36, 37 are in each case in fluid connection with the mixing chamber 39 via a corresponding fluid channel 51, 63. Moreover, a valve 64 is arranged in each fluid channel 51, 63 in proximity to the mixing chamber 39. Said valves 64 prevent a pushing of fluid 6, 8 from the mixing chamber 39 into the fluid channels 51, 63 during a downward movement of the piston 41. It should be noted here that such valves 64 can be present in any fluid channel in order to prevent an unwanted pulling of fluid 6, 8 out of the first and the second receptacles 16, 17 and into the mixing chamber 39 and/or the dispensing chamber 40, and/or an unwanted pushing of fluid 6, 8 from the mixing chamber 39 and/or the dispensing chamber 40 and into the fluid channels, respectively. For example, and although not depicted, it is conceivable that a valve is arranged in the fluid channel 51, 54 that connects the micropump 36 with the mixing chamber 39 and/or the second receptacle 17 with the dispensing chamber 40 of the fluid dispenser 1 according to FIGS. 12 and 13. These valves are preferably actuatable by the dispensing arrangement 38.

Figure 15:
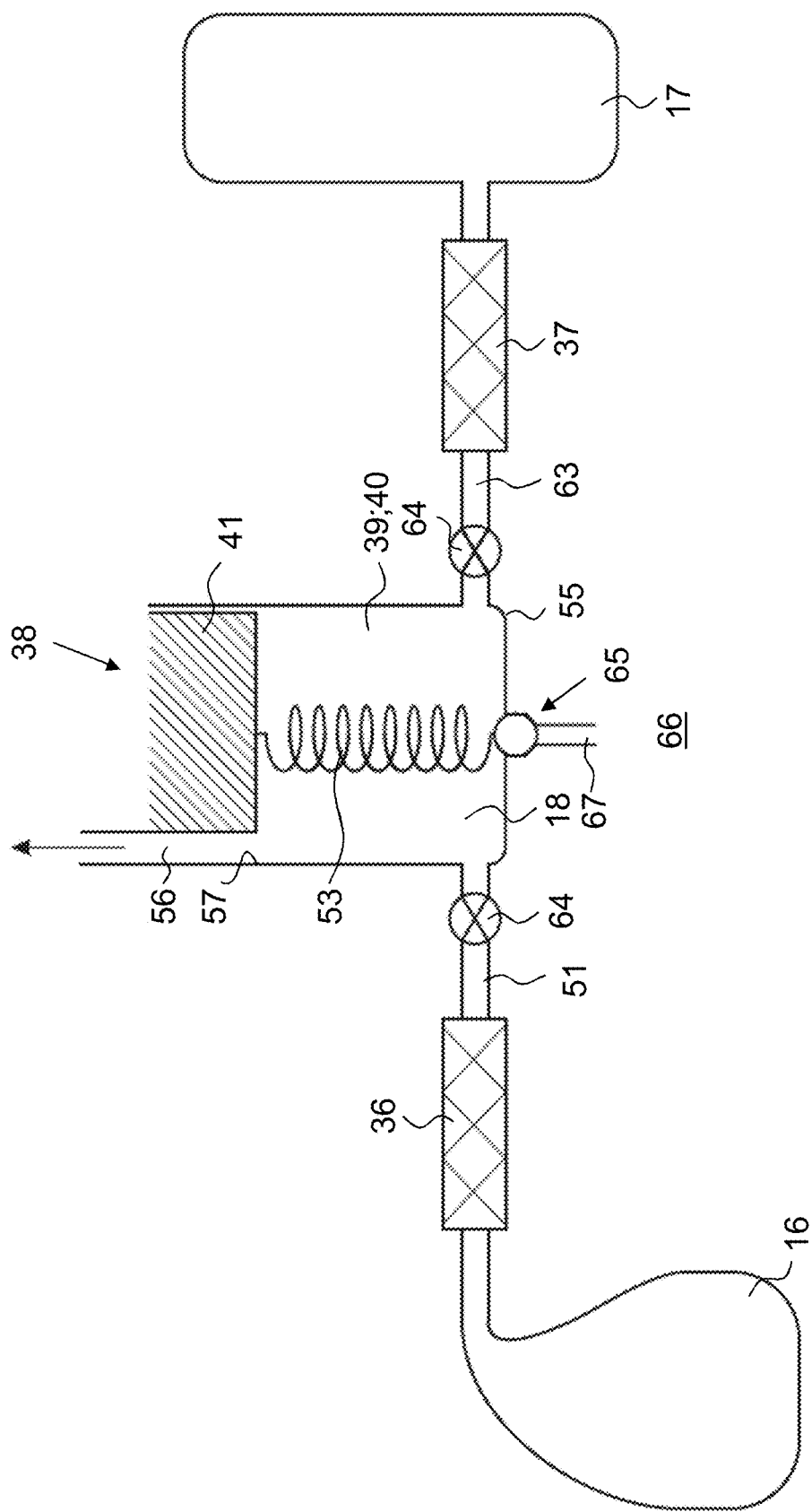
FIG. 15 shows a sectional view of a dispensing arrangement, a first dosing arrangement and a second dosing arrangement of a fluid dispenser according to a further aspect.
Figure 16:
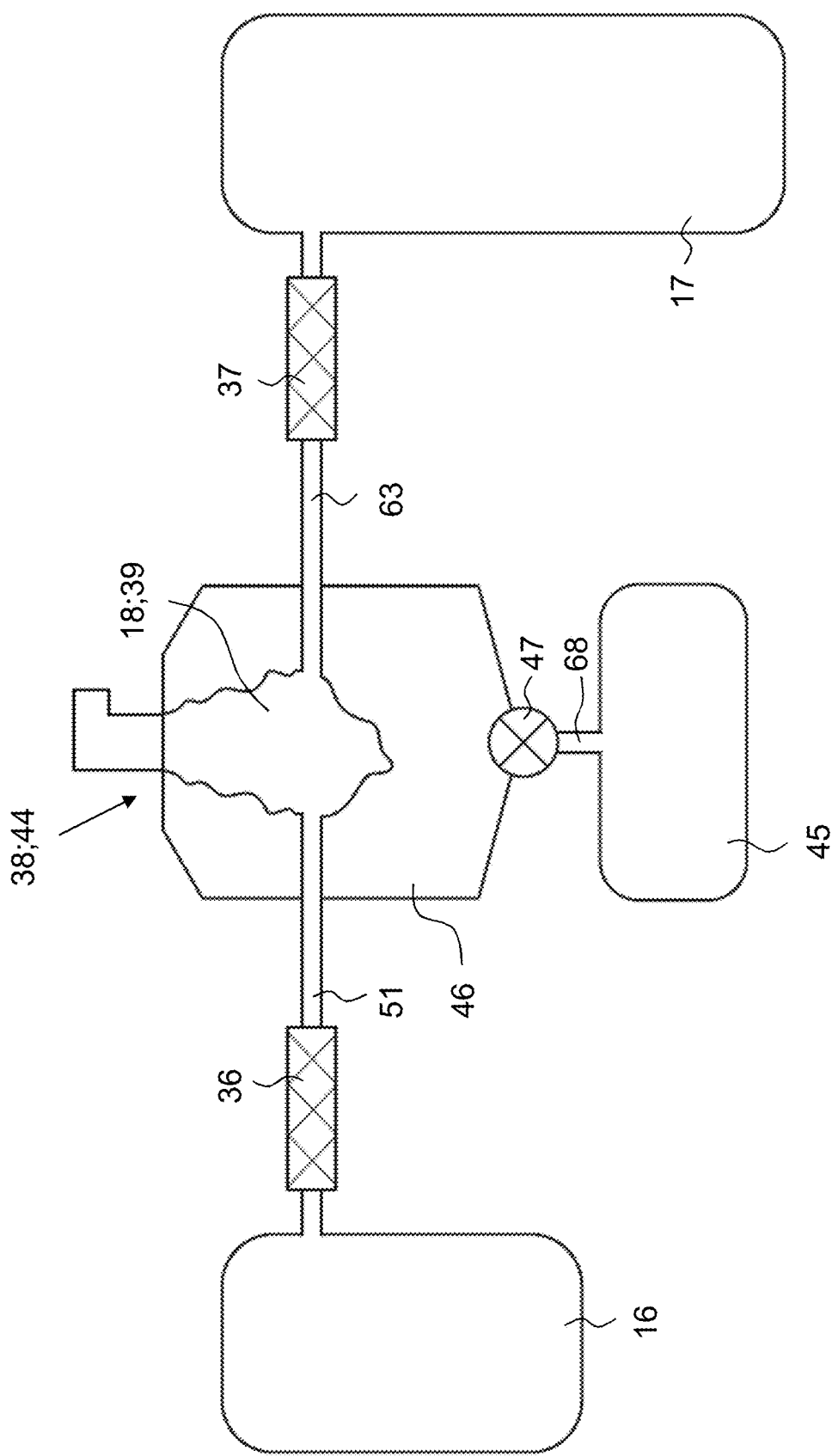
FIG. 16 shows a sectional view of a dispensing arrangement, a first dosing arrangement and a second dosing arrangement of a fluid dispenser according to a further aspect.

The embodiments depicted in FIGS. 15 and 16 comprise in each case a second dosing arrangement 37 in the form of a micropump. Moreover, the first and second dosing arrangements 36, 37 are in each case connected to the mixing chamber 39 by means of a fluid channel 51, 63. Each fluid channel 51, 63 comprises a valve 64 that prevents an unwanted pushing of fluid 6, 8 from the mixing chamber 39 into the receptacles 16, 17 or pulling of fluid 6, 8 from the receptacles 16, 17 into the mixing chamber 39, respectively. In the embodiment according to FIG. 15, the dispensing arrangement 38 comprises a dispensing chamber 40 and a spring-loaded piston 41 that is movably arranged within the dispensing chamber 40. As readily follows from FIG. 15, the dispensing chamber 40 corresponds to the mixing chamber 39. Hence, upon actuation of the dispensing arrangement 38, the micropumps 36, 37 are actuated such that doses of the first fluid 6 and of the second fluid 8 are allowed to flow into the dispensing chamber 40, i.e. the mixing chamber 39, whereby the cosmetic composition 2 is generated. Said cosmetic composition 2 can then be dispensed from the dispensing chamber 40 upon actuation of the piston 41, wherein the cosmetic composition 2 flows through a fluid channel 56 that is formed between an inner wall 57 of the dispensing chamber 40 and the piston 41. In contrast to the embodiments of FIGS. 12 and 13, the fluid dispenser 1 according to FIG. 15 comprises a first balancing arrangement 65 which enables a fluid communication between the dispensing chamber 40, i.e. the mixing chamber 39, and an exterior 66 of the mixing chamber 39, i.e. the dispensing chamber 40. The exterior 66 of the mixing chamber 39 (dispensing chamber 40) comprises a balancing fluid such as ambient air. The first balancing arrangement 65 corresponds here to a valve with a ball 52 that is arranged within a fluid channel 67 that connects the mixing chamber 39 (dispensing chamber 40) with the exterior 66. After the dispensing of the cosmetic composition 2 from the mixing chamber 39 (dispensing chamber 40), wherein the piston 41 has been moved downward towards the bottom wall 55 of the dispensing chamber 40, the spring-loaded design of the piston 41 will automatically push the piston 41 upward again. During this upward movement, the first balancing arrangement 65 is actuated, wherein balancing fluid is pulled from the exterior 66 into the mixing chamber 39 (dispensing chamber 40) as a result of capillary forces or a pressure difference caused by the moving piston 41 analogous to the situation that has been described with reference to FIGS. 12 and 13. Consequently, in a rest state, i.e. after an actuation but before any further actuation of the dispensing arrangement 38, balancing fluid will be present in the mixing chamber 39 (dispensing chamber 40).

The mixing chamber 39 of the fluid dispenser 1 according to FIGS. 12 to 15 in each case comprises or consists of a rigid material. Furthermore, the mixing chamber 39 is configured as an integral part of the housing 3 or the dispenser head 4. This is in contrast to the mixing chamber 39 of the fluid dispenser 1 according to FIG. 16, which constitutes a component being separate from the housing 3 or the dispenser head 4 and which is formed of a flexible and compressible material. In the embodiment of FIG. 16 the first and second dosing arrangements 36, 37 correspond to micropumps which are connected to the mixing chamber 39 via respective fluid channels 51, 63. Upon an actuation of the dispensing arrangement 38, doses of the first and second fluids 6, 8 are generated by the micropumps 36, 37 and are allowed to flow into the mixing chamber 39 via the respective fluid channels 51, 63, whereby the cosmetic composition 2 is generated. The dispensing arrangement 38 of this embodiment comprises a pressure assembly 44 that is configured to exert a pressure onto the mixing chamber 39 upon actuation, whereby the cosmetic composition 2 is transferred from the mixing chamber 39 to the dispenser head 4. The pressure assembly 44 comprises a pressure element in the form of a fluid, a first pressure chamber 45 and a second pressure chamber 46 which are in fluid communication with one another via a second balancing arrangement 47. The second balancing arrangement 47 corresponds here to a pump that is arranged within a fluid channel 68 connecting the first pressure chamber 45 to the second pressure chamber 46. The mixing chamber 39 is arranged within the second pressure chamber 46. The pressure assembly 44 is configured such, that at least part of the pressure element is transferred from the first pressure chamber into the second pressure chamber 46 upon actuation of the pressure assembly 44. In this way, the pressure element exerts a pressure onto the mixing chamber 39. Upon further actuation of the dispensing arrangement 38, such as pressing onto the dispenser head 4, the cosmetic composition 2 is transferred from the mixing chamber 39 to the dispenser head 4 and the pressure element is transferred back from the second pressure chamber 46 into the first pressure chamber 45.

Figure 17A:
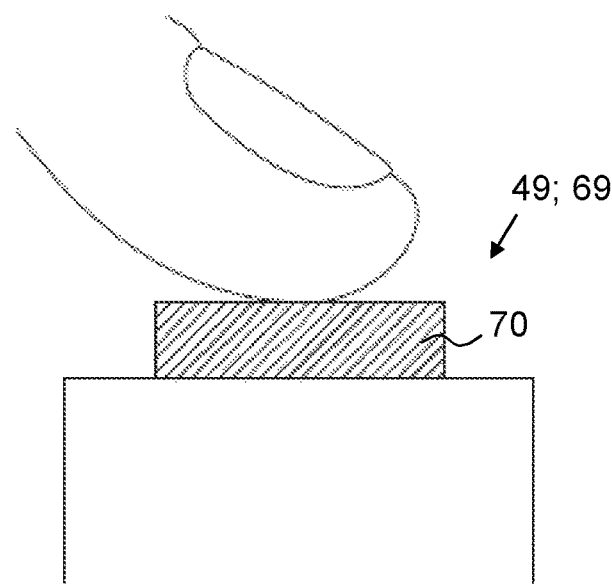
FIG. 17a shows a partial sectional view of an actuation arrangement of a dispensing arrangement in a first position.
Figure 17B:
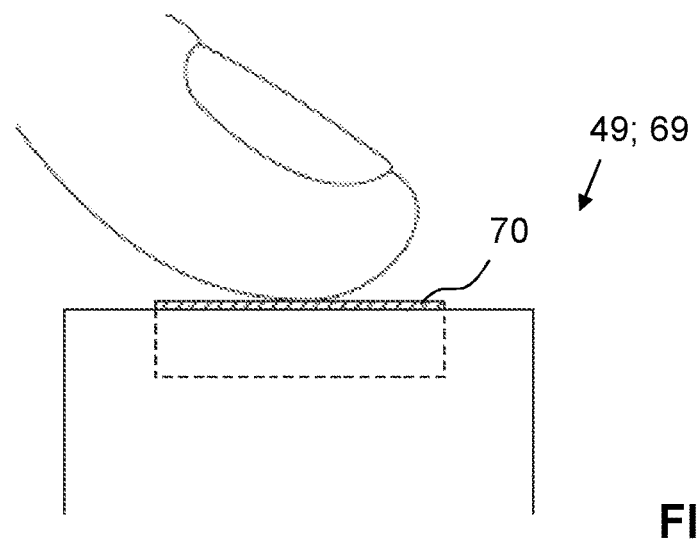
FIG. 17b shows a partial sectional view of the actuation arrangement of the dispensing arrangement according to FIG. 17a in a second position.
Figure 17C:
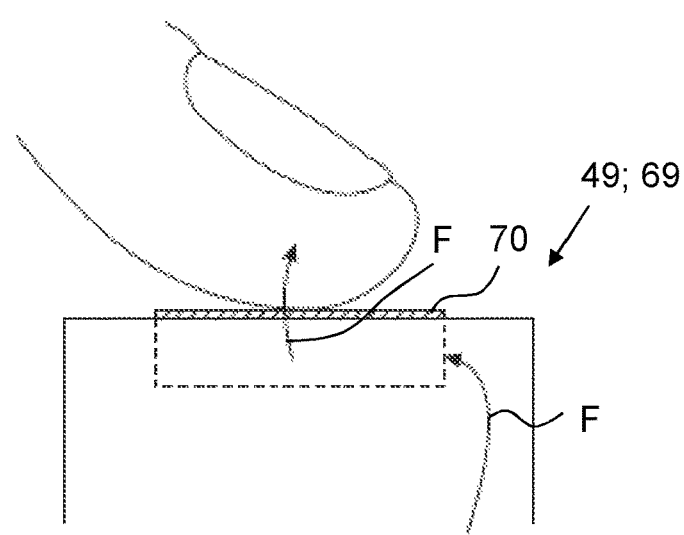
FIG. 17c shows a partial sectional view of the actuation arrangement of the dispensing arrangement according to FIG. 17a in a third position.

FIGS. 17a to 17c schematically illustrate a possible actuation of the dispensing arrangement 38. As has been mentioned previously, the dispensing arrangement 38 is configured such, that an actuation of the first dosing arrangement 36 and of the second dosing arrangement 37 in order to generate the dose of the first fluid 6 and the dose of the second fluid 8 occurs in a first step and that the transfer of the cosmetic composition 2 from the mixing area 18 to the dispenser head 4 occurs in a second step taking place after the first step as seen in time.

To this end it is preferred that the dispensing arrangement 38 comprises an actuation arrangement 69 that operates in stages and which is configured to provide a feedback F to a user. In FIGS. 17a to 17c the actuation arrangement 69 comprises an operating element 70 such as a button or switch which can be pressed by a user, see FIG. 17a, and which button or switch 70 is in connection with the first dosing arrangement 36 and the second dosing arrangement 37. Said button or switch 70 is configured such, that a first pressing by a user results in the actuation of the dosing arrangements 36, 37 in a first stage, whereby the doses of the first fluid 6 and of the second fluid 8 are generated, see FIG. 17b. After a preferably preset amount of time, which is indicative of a presence of the doses of the first fluid and of the second fluid in the mixing area, the actuation arrangement provides a feedback F to the user, see FIG. 17c. In response to the feedback F, the user can then actuate a second stage of the actuation arrangement 69, whereupon the dispensing arrangement 38 transfers the cosmetic composition 2 from the mixing area 18 to the dispenser head 4 in a second step. The actuation according to this second stage can be effectuated in various ways. For example, in the event that the dispensing arrangement 38 comprises an actuating element 41 in the form of a movable piston (see FIGS. 12-15), the actuation of the second stage of the actuation arrangement 69 corresponds to a mechanical actuation of the dispenser head 4. Namely, the dispenser head 4 is pushed downwards, wherein said movement is transferred onto the piston 41, whereby the cosmetic composition 2 is dispensed from the mixing chamber 39. To this end it is preferred that the button or switch 70 is arranged on the dispenser head 4, wherein the actuation arrangement 69 also comprises the dispenser head 4. However, it is likewise conceivable that the button or switch 70 is arranged on other parts of the fluid dispenser 1, for example on an outside of the housing 3. In the event that the dispensing arrangement 38 comprises a pressure assembly 44 (see FIG. 16), it is preferred that the actuation of the second stage of the actuation arrangement 69 corresponds to a mechanical and a non-mechanical, preferably electrical actuation of the pressure assembly 44, wherein the mechanical actuation takes place by pressing or moving the dispenser head 4 downwards and the non-mechanical actuation takes place by an actuation of the second balancing arrangement 47, wherein the second balancing arrangement 47 effectuates a transfer of the pressure element from the second pressure chamber 46 back into the first pressure chamber 45. To this end it is preferred that the button or switch 70 is further configured to actuate the pressure assembly 44 such, that the pressure element is transferred from the first pressure chamber 45 into the second pressure chamber 46 and vice versa. Said button or switch 70 can be arranged on the dispenser head 4 or on any other part of the fluid dispenser 1, such as on the outside of the housing 3.

Figure 18:
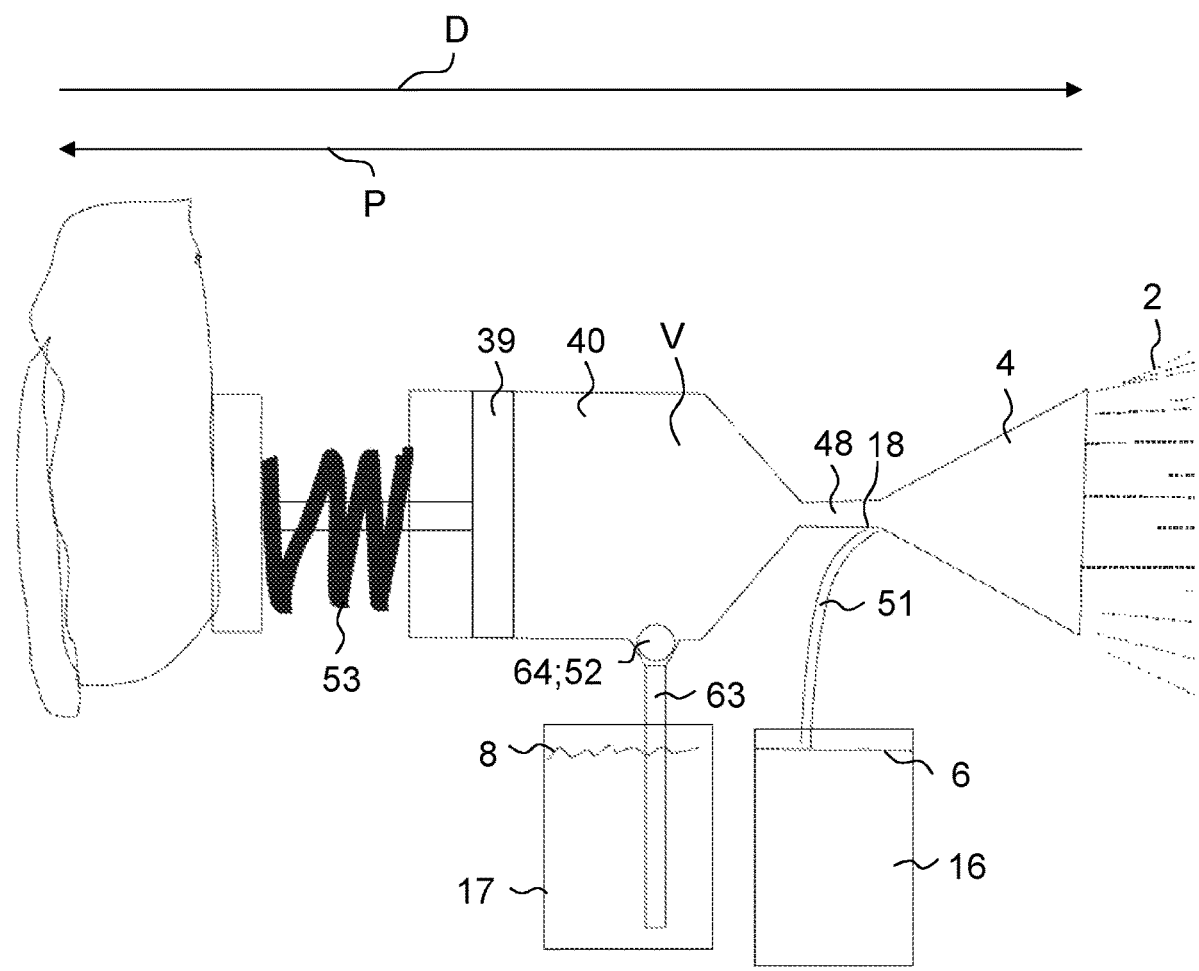
FIG. 18 shows a sectional view of a fluid dispenser comprising a dispensing arrangement, a first dosing arrangement and a second dosing arrangement according to a further aspect.

FIG. 18 depicts another embodiment of a dispensing arrangement 38, which comprises a dispensing chamber 40 and an actuating element 41 that is displaceably arranged within the dispensing chamber 40. Here, the actuating element 41 is a spring-loaded piston, wherein the piston 41 is arranged within the dispensing chamber 40 and is in operative connection with a spring 53 being arranged outside the dispensing chamber 40. The dispensing chamber 40 is in fluid communication with the first receptacle 16 and the second receptacle 17 via a respective fluid channel 51, 63. The dispensing chamber 40 is further in fluid communication with the dispenser head 4 and a venturi nozzle 48. The venturi nozzle 48 corresponds to a pipe or tube which effectuates a venturi effect, i.e. a reduction in fluid pressure when the first fluid 6 and/or the second fluid 8 flows through said pipe or tube 48. In the present example the pipe or tube constituting the venturi nozzle 48 is arranged between the dispensing chamber 40 and the dispenser head 4. As follows from FIG. 18 the fluid channel 51 being in connection with the first receptacle 16 merges into the venturi nozzle 48, whereby the mixing area 18 is provided within the venturi nozzle 48 in a region where said fluid channel 51 merges into the venturi nozzle 48. The fluid channel 63 being in connection with the second receptacle 17, however, is connected to the dispensing chamber 40. Within the dispensing chamber 40, in a region where the fluid channel 63 being in connection with the second receptacle 17 merges into the dispensing chamber 40, there is arranged a valve 64 with a ball 52. As outlined above, said valve 64 prevents an unwanted pushing of fluid 6, 8 from the dispensing chamber 40 into the second receptacle 17 during an actuation of the piston 41. If a user actuates the dispensing arrangement 38 by pulling the actuating element 41 along a proximal direction P such, that a volume V within the dispensing chamber 40 and being delimited by the actuating element 41 is increased, a dose of second fluid 8 is pulled from the second reservoir 7 into the dispensing chamber 40 in a first step. If the user then further actuates the dispensing arrangement 38 by pushing the actuating element 41 along a distal direction D running opposite to the proximal direction P, the second fluid 8 is dispensed from the dispensing chamber 40 towards the dispenser head 4 via the venturi nozzle 48. During the flow of second fluid 8 through the venturi nozzle 48, a dose of first fluid 6 is pulled from the first receptacle 16 into the venturi nozzle 48 as a result of the venturi effect. Thereby, the cosmetic composition 2 is generated within the venturi nozzle 48. During said pushing movement of the actuation element 41 along the distal direction D the cosmetic composition 2 is not only generated but also readily dispensed from the dispenser head 4. Different dispensing cycles are associated with these different embodiments. A dispensing cycle is understood here as the process of actuating the first dosing arrangement 36 so as to generate the dose of the first fluid 6, which dose will then flow into the mixing area 18, and of transferring the cosmetic composition 2 from the mixing area 18 to the dispenser head 4 for dispensing. The dispensing cycles associated with the embodiments depicted in FIGS. 12 and 13 are as follows. Namely, a staggered actuation of the first dosing arrangement 36 and the second dosing arrangement 37 takes place during two subsequent dispensing cycles. In this case, in an initial state of the dispensing cycle, a dose of the second fluid 8 has already been generated because of the second dosing arrangement 37 being provided by means of a piston pump, which automatically pulls a dose of the second fluid 8 from the second receptacle 17 into the mixing chamber 39 (FIG. 12) or into the dispensing chamber 40 (FIG. 13) after an actuation of the dispensing arrangement 38 in a previous dispensing cycle. If a user wants to apply the cosmetic composition 2, he actuates the dispensing arrangement 38 in a first step, for example by pressing a button or switch 70 as mentioned above, wherein the dispensing arrangement 38 actuates the micropump 36 in order to generate a dose of the first fluid 6. Said dose will flow into the mixing area 18, wherein it can mix with the dose of the second fluid 8 that has been generated in the previous dispensing cycle, whereby the cosmetic composition 2 is generated. Once that the cosmetic composition 2 is generated, it can be dispensed from the fluid dispenser 1 in a second step taking place after the first step, for example by pushing the dispenser head 4 downwards. The generation of the cosmetic composition 2 by the embodiments depicted in FIGS. 14a to 16 takes place during the same dispensing cycle. Namely, either a staggered or simultaneous actuation of the first and second dosing arrangements 36, 37 in the form of the micropumps takes place in a first step, wherein doses of the first fluid 6 and the second fluid 8 are generated and allowed to flow into the mixing chamber 39, whereby the cosmetic composition 2 is generated. That is, in an initial state neither first fluid 6 nor second fluid 8 is present in the mixing chamber. The actuation of the micropumps 36, 37 is preferably achieved by means of a button or switch 70 which can be touched or pressed by a user as outlined above. Thereafter, the cosmetic composition 2 is dispensed from the mixing chamber 39, for example by pushing the dispenser head 4 downwardly (FIGS. 14a, 14b and 15) or by actuating the pressure assembly 44 (FIG. 16). In the case of the embodiment according to FIG. 18 a staggered actuation of the first and second dosing arrangements 36, 37 occurs, wherein the second dosing arrangement 37 being provided by the dispensing chamber 40 and the piston 41 is actuated in a first step by pulling the piston 41 along the proximal direction P and wherein the first dosing arrangement 36 being provided by the venturi nozzle 48 is actuated in a second step by pushing the piston 41 along the distal direction D. All embodiments discussed herein have in common that the dispensing arrangement 38 is configured such, that the mixing area 18 comprises both the first fluid 6 and the second fluid 8 only in the event that the dispensing arrangement 38 has been actuated. In other words, the cosmetic composition 2 is generated only in the event of an actuation by a user.

The invention claimed is:

1. A fluid dispenser for dispensing a cosmetic composition comprising:
   a housing;
   a dispenser head being arranged on the housing and being configured to dispense the cosmetic composition from the fluid dispenser;
   at least one first receptacle being provided in the housing, the first receptacle being connectable to a first reservoir comprising a first fluid; and
   at least one second receptacle being provided in the housing, the second receptacle being connectable or connected to a second reservoir, the second reservoir being configured to receive a second fluid;
   wherein the fluid dispenser further comprises a mixing area being in fluid communication with the dispenser head, the first receptacle and the second receptacle, and
   wherein the mixing area is configured such, that the cosmetic composition is generated when a dose of the first fluid is mixed with the second fluid within the mixing area,
   wherein the fluid dispenser further comprises:
      at least a dispensing arrangement; and
      at least a first dosing arrangement and at least a second dosing arrangement;
   wherein the dispensing arrangement is configured to actuate the first dosing arrangement and the second dosing arrangement upon its actuation by a user of the fluid dispenser,
   wherein the first dosing arrangement is in fluid communication with the first receptacle and the mixing area,
   wherein the second dosing arrangement is in fluid communication with the second receptacle and the mixing area,
   wherein the first dosing arrangement is configured to generate upon actuation by the dispensing arrangement, upon receipt of a first dosing arrangement trigger signal that is produced by the dispensing arrangement, the dose of the first fluid, and
   wherein the second dosing arrangement is configured to generate upon actuation by the dispensing arrangement, upon receipt of a second dosing arrangement trigger signal that is produced by the dispensing arrangement, a dose of the second fluid,
   wherein the fluid dispenser further comprises at least one power supply configured to supply power to at least one of: the dispensing arrangement, the first dosing arrangement, and the second dosing arrangement,
   wherein at least one of:
   i) the first dosing arrangement is configured to prepare the dose of the first fluid at least one of a) in the range of between 1 microliter to 200 microliter and b) less than 40 microliter and the second dosing arrangement is configured to prepare the dose of the second fluid at least one of a) in the range of between 1 microliter to 200 microliter and b) less than 40 microliter, and ii) the first dosing arrangement and the second dosing arrangement is a micropump,
wherein the dispensing arrangement and the first dosing arrangement are configured separately from one another and are in fluid connection with one another via a fluid channel, and
wherein the dispensing arrangement and the second dosing arrangement are configured separately from one another and are in fluid connection with one another via a fluid channel.

2. The fluid dispenser according to claim 1, wherein the fluid dispenser is configured such, that the cosmetic composition is generated essentially immediately before it is dispensed.

3. The fluid dispenser according to claim 1, wherein the fluid dispenser is configured to generate droplets of the first fluid.

4. The fluid dispenser according to claim 3, wherein the mixing area is configured to generate droplets of the first fluid.

5. The fluid dispenser according to claim 1, wherein the dispensing arrangement is configured such, that the first dosing arrangement and the second dosing arrangement are actuated simultaneously or temporally delayed with respect to one another.

6. The fluid dispenser according to claim 1, wherein the dispensing arrangement is configured such, that the mixing area comprises both the first fluid and the second fluid only in the event that the dispensing arrangement has been actuated.

7. The fluid dispenser according to claim 1, wherein the dispensing arrangement is further configured to transfer the cosmetic composition from the mixing area to the dispenser head for dispensing.

8. The fluid dispenser according to claim 7, wherein the dispensing arrangement is configured such, that an actuation of at least one of i) the first dosing arrangement and ii) of the second dosing arrangement in order to generate at least one of i) the dose of the first fluid and ii) the dose of the second fluid occurs in a first step and the transfer of the cosmetic composition from the mixing area to the dispenser head occurs in a second step taking place after the first step as seen in time.

9. The fluid dispenser according to claim 1, wherein the dispensing arrangement comprises the mixing area.

10. The fluid dispenser according to claim 1, wherein at least one of i) the first dosing arrangement is provided in the housing or on the first reservoir or in the first reservoir or in the dispenser head, and
ii) wherein the second dosing arrangement is provided in the housing or on the second reservoir or in the second reservoir or in the dispenser head.

11. The fluid dispenser according to claim 1, wherein the mixing area is provided within a mixing chamber, and wherein the first receptacle, the second receptacle and the dispenser head are in fluid communication with the mixing chamber.

12. The fluid dispenser according to claim 11, wherein the mixing chamber is arranged within the housing or within the dispenser head.

13. The fluid dispenser according to claim 11, wherein the mixing chamber comprises at least one of i) a rigid material or a flexible material and ii) a compressible material.

14. The fluid dispenser according to claim 11,
wherein the dispensing arrangement comprises at least one pressure assembly that is configured to exert a pressure onto the mixing chamber upon actuation, whereby the cosmetic composition is transferable from the mixing chamber to the dispenser head.

15. The fluid dispenser according to claim 14,
wherein the pressure assembly comprises a pressure element such as a fluid, at least a first pressure chamber and a second pressure chamber which are in fluid communication with one another,
wherein the mixing chamber is arranged within the second pressure chamber, and
wherein the pressure assembly is configured such, that at least part of the pressure element is transferred from the first pressure chamber into the second pressure chamber upon actuation of the pressure assembly, whereby the cosmetic composition is transferable from the mixing chamber to the dispenser head.

16. The fluid dispenser according to claim 1,
wherein the dispensing arrangement comprises a dispensing chamber and an actuating element that is arranged within the dispensing chamber, wherein the dispensing chamber is in fluid communication with the mixing chamber and the dispenser head, and
wherein the dispensing arrangement is configured such, that the cosmetic composition is transferable from the mixing chamber to the dispenser head upon an actuation of the actuating element.

17. The fluid dispenser according to claim 16,
wherein the dispensing chamber corresponds to the mixing chamber, or
wherein the dispensing chamber and the mixing chamber are configured separately from one another and are in fluid connection with one another.

18. The fluid dispenser according to claim 16,
wherein the dispensing arrangement is configured such, that the second fluid is transferable from the second reservoir into the mixing chamber after the actuation of the actuating element, or
wherein the fluid dispenser further comprises at least a first balancing arrangement which enables a fluid communication between the mixing chamber and an exterior of the mixing chamber, and wherein the first balancing arrangement is configured such, that a balancing fluid is transferable from the exterior of the mixing chamber into the mixing chamber after the actuation of the actuating element.

19. The fluid dispenser according to claim 16, wherein the actuating element is displaceably mounted within the dispensing chamber, and wherein the dispenser head is spring-loaded and displaceably arranged on the housing; or
wherein the actuating element is spring-loaded and displaceably mounted within the dispensing chamber.

20. The fluid dispenser according to claim 19, wherein the actuating element is a piston.

21. The fluid dispenser according to claim 1, further comprising a droplet generator, the droplet generator being in fluid communication with the dispenser head, the first receptacle and the second receptacle and being configured to generate droplets of the first fluid when the first fluid flows in said droplet generator; and
wherein the droplet generator comprises the mixing area, or
wherein the droplet generator is in fluid communication with the mixing area.

22. The fluid dispenser according to claim 1,
wherein the mixing area is in fluid communication with the first receptacle and the second receptacle via a first fluid channel and a second fluid channel, respectively, and wherein the first fluid channel merges into the second fluid channel within the mixing area, such that droplets of the first fluid being dispersed in the second fluid and thereby the cosmetic composition are generated.

23. The fluid dispenser according to claim 22,
wherein the first receptacle and the droplet generator are in fluid communication via a first fluid channel,
wherein the second receptacle and the droplet generator are in fluid communication via a second fluid channel, and
wherein the droplets of the first fluid generated in the droplet generator are dispersed from the droplet generator into the second fluid flowing in the second fluid channel, whereby the cosmetic composition is generated.

24. The fluid dispenser according to claim 23, wherein the droplet generator comprises a piezoelectric element, and wherein the droplets of the first fluid are generated in the droplet generator upon activation of the piezoelectric element.

25. The fluid dispenser according to claim 22, wherein the droplet generator is a microfluidic device.

26. The fluid dispenser according to claim 1, further comprising at least one selection device being in communication with at least one of: the first receptacle, the first reservoir when in connection with the first receptacle, the second receptacle, the second reservoir when in connection with the second receptacle, the first dosing arrangement, the second dosing arrangement, and the droplet generator such that at least one of a selected dose of the first fluid is dispensed from the first receptacle, a selected dose of the first fluid is dispensed from the first reservoir, a selected dose of the second fluid is dispensed from the second receptacle, a selected dose of the second fluid is dispensed from the second reservoir, a selected dose of the first fluid is generated by the first dosing arrangement, a selected dose of the second fluid is generated by the second dosing arrangement and a selected dose of droplets of the first fluid is generated in the droplet generator,
wherein the selection device is adjustable between at least a first selection mode and a second selection mode.

27. The fluid dispenser according to claim 1, wherein at least one of i) the first fluid is selected from the group consisting of one or more fragrant essential oils, one or more aroma compounds, or mixtures thereof, and
ii) wherein the second fluid corresponds to an aqueous solution.

28. The fluid dispenser according to claim 1, wherein at least one of i) the first reservoir is provided in the form of a first container that is removably connectable to the first receptacle; and
ii) wherein the second reservoir is provided in the form of a second container that is removably connectable to the second receptacle, or
wherein the second reservoir is connected to the second receptacle and is an integral part of the housing.

29. The fluid dispenser according to claim 1, further comprising at least one of i) at least one activation device and ii) an actuation arrangement, the activation device being configured to transmit an activation signal to at least one of: the first receptacle, the first reservoir when in connection with the first receptacle, the second receptacle, the second reservoir when in connection with the second receptacle, the droplet generator, and the dispenser head such that at least one of a release of the first fluid from the first receptacle, a release of the first fluid from the first reservoir, a release of the second fluid from the second receptacle, a release of the second fluid from the second reservoir, a release of droplets of the first fluid from the droplet generator and a dispensing of the cosmetic composition from the fluid dispenser is enabled, the actuation arrangement being configured to actuate at least one of the first dosing arrangement, the second dosing arrangement, the pressure assembly such that at least one of a generation of droplets of the first fluid by the first dosing arrangement, a generation of droplets of the second fluid by the second dosing arrangement and a transfer of the cosmetic composition from the mixing chamber to the dispenser head by the pressure assembly is enabled.

30. The fluid dispenser according to claim 29, wherein the power supply configured to supply power to at least one of: the activation device, the first receptacle, the first reservoir when in connection with the first receptacle, the second receptacle, the second reservoir when in connection with the second receptacle, the actuation arrangement, the dispensing arrangement, the first dosing arrangement, the second dosing arrangement, the pressure assembly, the droplet generator, and the dispenser head, and
ii) further comprising at least one level indicator being at least one of configured to indicate the amount of the first fluid in the first reservoir, being configured to indicate the amount of second fluid in the second receptacle, being configured to indicate the amount of first fluid in the mixing chamber, being configured to indicate the amount of second fluid in the mixing chamber, and being configured to indicate the amount of cosmetic composition in the mixing chamber.

31. The fluid dispenser according to claim 1, wherein the housing is comprised of at least a first housing part and a second housing part, wherein the first housing part and the second housing part of the housing are designed to be rotatable with respect to one another, and wherein the first receptacle is arranged in the first housing part of the housing and the second receptacle is arranged in the second housing part of the housing.

32. The fluid dispenser according to claim 1, wherein at least one of i) the fluid dispenser is a perfume dispenser and ii) the cosmetic composition is a perfume.

33. The fluid dispenser according to claim 1, wherein the dispenser head is in fluid connection with the mixing area.

* * * * *